United States Patent
Zhao et al.

(10) Patent No.: US 9,062,087 B2
(45) Date of Patent: Jun. 23, 2015

(54) PHENYL C-GLUCOSIDE DERIVATIVES, PREPARATION METHODS AND USES THEREOF

(75) Inventors: Guilong Zhao, Tianjin (CN); Hua Shao, Tianjin (CN); Weiren Xu, Tianjin (CN); Wei Liu, Tianjin (CN); Yuli Wang, Tianjin (CN); Lida Tang, Tianjin (CN); Chubing Tan, Tianjin (CN); Bingni Liu, Tianjin (CN); Shijun Zhang, Tianjin (CN)

(73) Assignee: Tianjin Institute of Pharmaceutical Research, Tianjin (CN)

( * ) Notice: Subject to any disclaimer, the term of this patent is extended or adjusted under 35 U.S.C. 154(b) by 193 days.

(21) Appl. No.: 13/575,258

(22) PCT Filed: Jan. 14, 2011

(86) PCT No.: PCT/CN2011/000061
§ 371 (c)(1),
(2), (4) Date: Oct. 10, 2012

(87) PCT Pub. No.: WO2011/091710
PCT Pub. Date: Aug. 4, 2011

(65) Prior Publication Data
US 2013/0023486 A1    Jan. 24, 2013

(30) Foreign Application Priority Data

Jan. 26, 2010  (CN) .......................... 2010 1 0101146
Oct. 27, 2010  (CN) .......................... 2010 1 0522337

(51) Int. Cl.
| C07H 7/04 | (2006.01) |
| C07H 7/06 | (2006.01) |
| A61K 31/70 | (2006.01) |
| A61K 31/351 | (2006.01) |
| C07D 309/10 | (2006.01) |
| C07D 409/10 | (2006.01) |

(52) U.S. Cl.
CPC .. C07H 7/04 (2013.01); C07H 7/06 (2013.01); A61K 31/351 (2013.01); A61K 31/70 (2013.01); C07D 309/10 (2013.01); C07D 409/10 (2013.01)

(58) Field of Classification Search
CPC .. C07D 309/10; C07D 409/10; C07D 405/10; C07D 407/10
See application file for complete search history.

(56) References Cited

U.S. PATENT DOCUMENTS 6,515,117 B2 * 2/2003 Ellsworth et al. ............ 536/17.2
2006/0063722 A1   3/2006 Washburn
2008/0242596 A1 * 10/2008 Chen et al. .................... 514/4

FOREIGN PATENT DOCUMENTS

| CN | 1829729 A | 9/2006 |
| CN | 101065391 A | 10/2007 |
| CN | 101503399 A | 8/2009 |
| JP | 2004-359630 A | 12/2004 |
| WO | 2005/012326 A1 | 2/2005 |

OTHER PUBLICATIONS

Chen et al., CN 101503399 A, Aug. 2009, machine translation, retrieved on Mar. 27, 2014 from http://search.proquest.com/professional/docview/1358598902/fulltext/14469BAA0CA6B03D41F.*
Strunecká, A., Patočka, J., & Connett, P. (2004). Fluorine in medicine. J Appl Biomed, 2, 141-150.*
Lima, L. M., & Barreiro, E. J. (2005). Bioisosterism: a useful strategy for molecular modification and drug design. Current medicinal chemistry, 12(1), 23-49.*
Tomiyama et al., JP 2004359630 A, Dec. 2004, machine translation, Retrieved on Aug. 18, 2014 from http://worldwide.espacenet.com.*
International Preliminary Report on Patentability mailed Jul. 31, 2012, issued in corresponding International Application No. PCT/CN2011/000061, filed Jan. 14, 2011, 9 pages.
International Search Report and Written Opinion mailed Apr. 14, 2011, issued in corresponding International Application No. PCT/CN2011/000061, filed Jan. 14, 2011, 13 pages.

* cited by examiner

*Primary Examiner* — Shaojia Anna Jiang
*Assistant Examiner* — Dale R Miller
(74) *Attorney, Agent, or Firm* — Christensen O'Connor Johnson Kindness PLLC

(57) ABSTRACT

The present invention relates to a sodium glucose cotransporter 2 (SGLT2) inhibitor with a phenyl C-glucoside structure, its preparation method, a pharmaceutical composition containing the same, and its use in treating diabetes and preparing an anti-diabetes medicament. The invention provides a compound with the structure of general formula I and a pharmaceutically acceptable salt and prodrug ester thereof, wherein, the definitions of $R^5$ and $R^6$ are selected from the following:
(1) R5=R6=Me; (2) R5=Me, R6=OMe; (3) R5=Me, R6=H; (4) R5=Me, R6=F; (5) R5=F, R6=H; and (6) R5=OMe, R6=H.

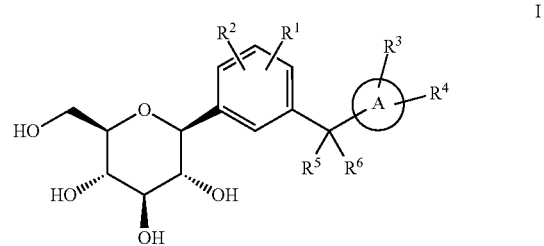

14 Claims, No Drawings

PHENYL C-GLUCOSIDE DERIVATIVES, PREPARATION METHODS AND USES THEREOF

TECHNICAL FIELD

The present invention relates to the field of related drugs for diabetes. In particular, this invention relates to sodium glucose cotransporter 2 (SGLT2) inhibitors with phenyl C-glucoside structures which are effective in treating diabetes, their preparation methods, and pharmaceutical compositions containing the same.

BACKGROUND ART

So far there are 170 million diabetes patients all over the world, and most of them are Diabetes II patients (i.e., non-insulin-dependent type). Now the anti-diabetes medicines for clinical use mainly include Metformins, sulfonylureas, insulins, thiazolidinediones, α-glucosidase inhibitors and dipeptidyl peptidase-IV inhibitors. Although these medicines are effective in treatments, there exists safety concern for long term treatment, e.g., hepatotoxicity, and some of them will cause many problems such as weight gain.

Sodium glucose cotransporter 2 (SGLT2) has been discovered to be a new target for treating diabetes in recent years. SGLT2 is mainly distributed in renal proximal tubules, and serves to absorb the glucose in urine and return it back to blood. So, inhibiting SGLT2 can result in decreased glucose concentration in blood, which decreases blood glucose level by a pathway different from previous ones. More glucose will be secreted into urine when the function of SGLT2 is inhibited, which helps diabetes patients to keep normal blood glucose level. Since SGLT2 inhibitors are not involved in glucose metabolism, they may serve as a supplementary means of dominant methods for controlling blood glucose.

Chinese patent application No. CN200610093189.9 discloses a compound with the following structure as a SGLT2 inhibitor:

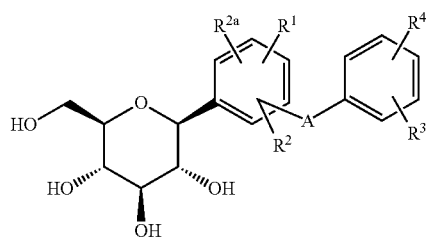

wherein A is O, S, NH, $(CH_2)_n$, wherein n=0 to 3.

Chinese patent application No. CN200380110040.1 discloses a compound with the following structure as a SGLT2 inhibitor:

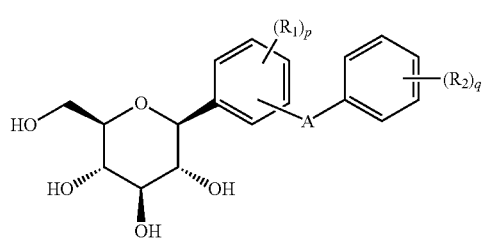

wherein A is a covalent bond, O, S, NH, $(CH_2)_n$, wherein n=1 to 3.

Chinese patent application No. CN200480006761.2 discloses a compound with the following structure as a SGLT2 inhibitor:

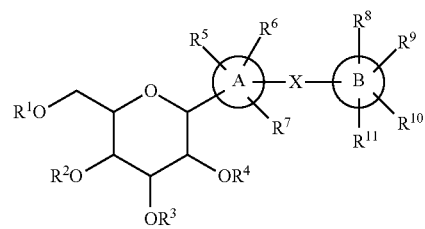

wherein X is a covalent bond or a lower alkylene group.

WO 2005/012326 discloses a compound with the following structure as a SGLT2 inhibitor:

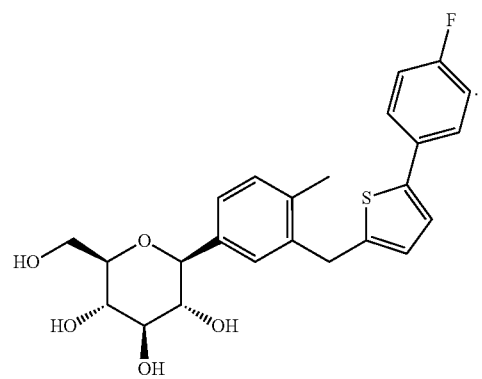 [SMILES: Cc1ccc([C@@H]2O[C@H](CO)[C@@H](O)[C@H](O)[C@H]2O)cc1Cc1ccc(-c2ccc(F)cc2)s1]

SUMMARY OF THE INVENTION

To overcome the disadvantages and shortcomings of the prior art, one object of the present invention is to provide a SGLT2 inhibitor with good activity, which is phenyl C-glucoside with the structure of general formula I and its pharmaceutically acceptable salt and prodrug ester.

Another object of the present invention is to provide a method for preparing a phenyl C-glucoside with the structure of general formula I.

Yet another object of this invention is to provide a pharmaceutical composition comprising a compound of general formula I or a pharmaceutically acceptable salt or prodrug ester thereof as an active ingredient, and one or more pharmaceutically acceptable carriers, excipients and/or diluents, and its use in inhibiting sodium glucose cotransporter 2, such as the use in treating diabetes.

The phenyl C-glucoside derivative provided by the present invention is a novel SGLT2 inhibitor, which serves as the basis for preparing a medicament which may be further used for treating diabetes, especially non-insulin-dependent diabetes mellitus.

DETAILED DESCRIPTION OF THE INVENTION

The invention is now described in detail in combination with the objects of the invention.

The present invention provides a compound with the structure of general formula I,

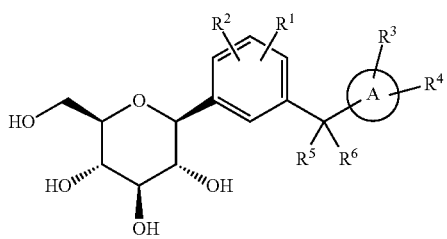

I

Wherein:

$R^1$, $R^2$, $R^3$ and $R^4$ are independently selected from the group consisting of H, F, Cl, Br, I, OH, $OR^7$, $SR^8$, $OCF_3$, $CF_3$, $CHF_2$, $CH_2F$, a $C_1$-$C_3$ alkyl and a cycloalkyl having 3 to 5 carbon atoms, wherein $R^7$ and $R^8$ are independently selected from a $C_1$-$C_3$ alkyl, and both of the aforesaid alkyl and cycloalkyl can be substituted by one or more atoms selected from F and Cl;

Ring A is selected from an aromatic monocycle and an aromatic bicycle, and the two rings in the aromatic bicycle can be either fused to form a fused ring or connected through a covalent bond as two independent aromatic rings. Both the aromatic monocycle and the aromatic bicycle are a 5- to 12-membered ring which can be substituted by 1 to 3 heteroatoms selected from O, S and N; ring A can be connected with other parts of compound I at any possible position;

the definitions of $R^5$ and $R^6$ are selected from the following:

(1) $R^5$=$R^6$=Me;
(2) $R^5$=Me, $R^6$=OMe;
(3) $R^5$=Me, $R^6$=H;
(4) $R^5$=Me, $R^6$=F;
(5) $R^5$=F, $R^6$=H;
(6) $R^5$=OMe, $R^6$=H.

Preferred compound with the structure of general formula I is as follows:
wherein,
$R^1$, $R^2$, $R^3$ and $R^4$ are independently selected from the group consisting of H, F, Cl, $OR^7$, $SR^8$, $OCF_3$, $CF_3$, $CHF_2$, $CH_2F$, a $C_1$-$C_3$ alkyl and a cycloalkyl having 3 to 5 carbon atoms, wherein $R^7$ and $R^8$ are independently selected from a $C_1$-$C_3$ alkyl, and both of the aforeasid alkyl and cycloalkyl can be substituted by one or more atoms selected from F and Cl atoms;

ring A is selected from an aromatic monocycle and an aromatic bicycle, and the two rings in the aromatic bicycle can be either fused to form a fused ring or connected through a covalent bond as two independent aromatic rings. Both the aromatic monocycle and aromatic bicycle are a 5- to 12-membered ring which can be substituted by one or two heteroatoms selected from O and S; ring A can be connected with other part of compound I at any possible position;

the definitions of $R^5$ and $R^6$ are selected from the following:

(1) $R^5$=$R^6$=Me;
(2) $R^5$=Me, $R^6$=H;
(3) $R^5$=Me, $R^6$=F;
(4) $R^5$=F, $R^6$=H.

More preferred compound with the structure of general formula I is as follows:
wherein,
$R^1$, $R^2$, $R^3$ and $R^4$ are independently selected from the group consisting of F, Cl, $OR^7$, $SR^8$, $OCF_3$, $CF_3$, $CHF_2$, $CH_2F$, a $C_1$-$C_3$ alkyl and a cycloalkyl having 3 to 4 carbon atoms, wherein $R^7$ and $R^8$ are independently selected from a $C_1$-$C_3$ alkyl, and both of the aforesaid alkyl and cycloalkyl can be substituted by one or more F atoms;

ring A is selected from the group consisting of benzene, benzothiophene, benzofuran, azulene, benzene and thiophene rings connected by a covalent bond in any possible form, and benzene and furan rings connected by a covalent bond in any possible form; ring A can be connected with other part of compound I at any possible position;

the definitions of $R^5$ and $R^6$ are selected from the following:

(1) $R^5$=$R^6$=Me;
(2) $R^5$=Me, $R^6$=H;
(3) $R^5$=F, $R^6$=H.

The structure of the most preferred compound with the structure of general formula I is as follows:

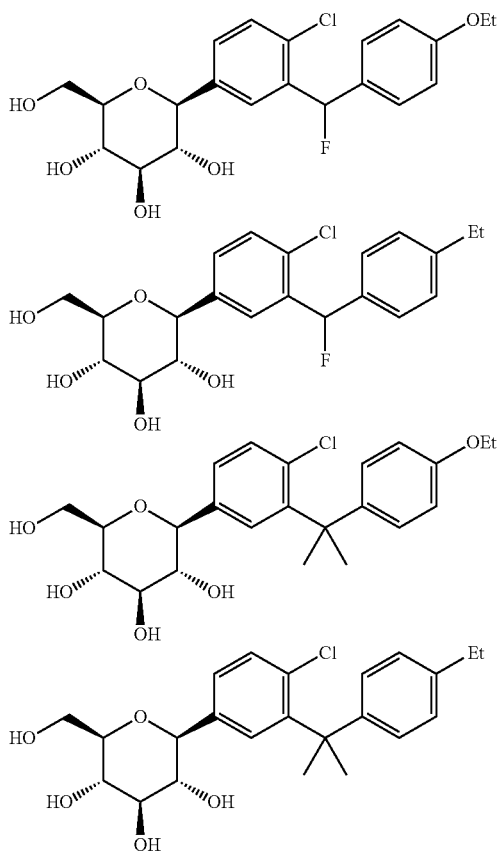

-continued

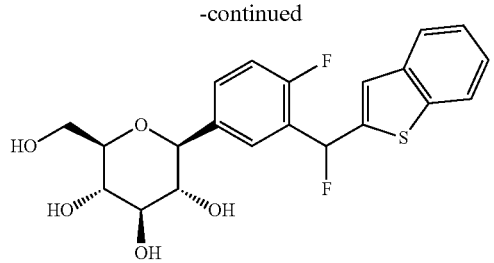
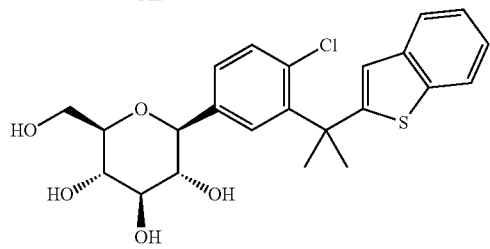
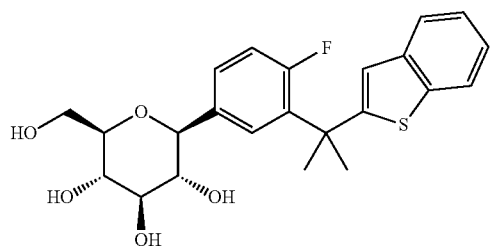
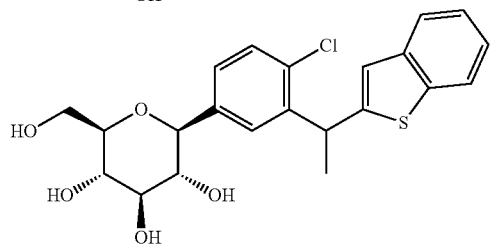
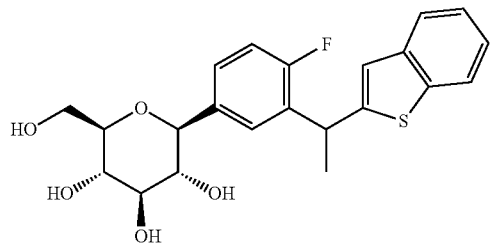
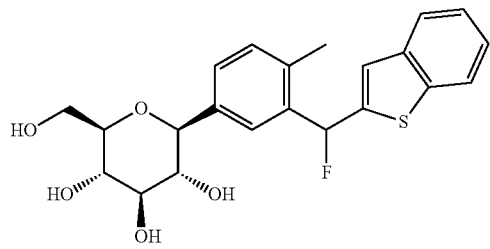
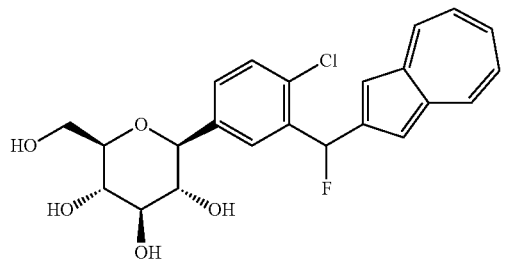
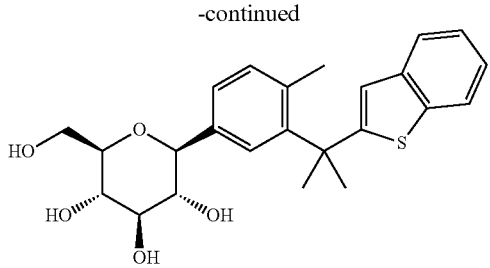
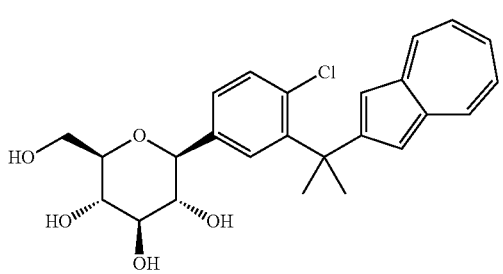
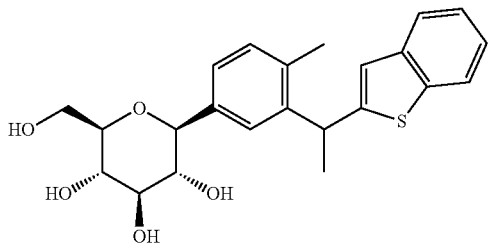
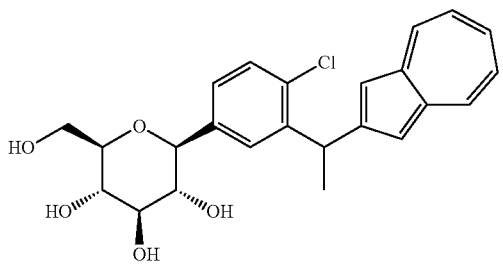
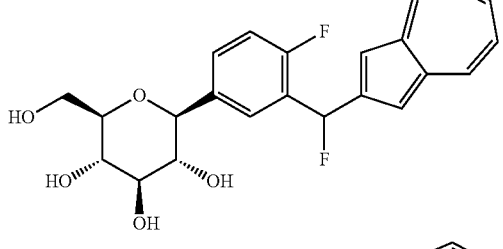
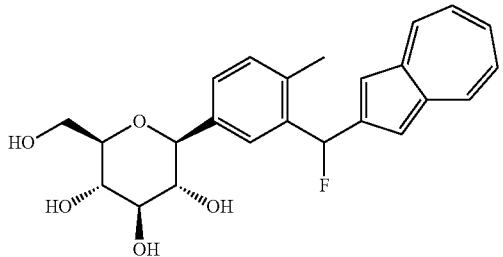

-continued
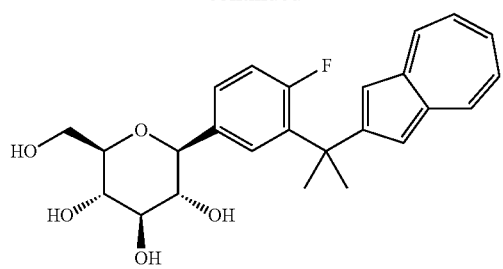
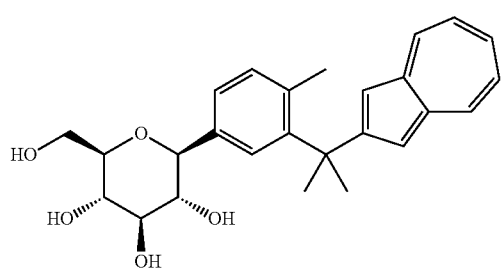
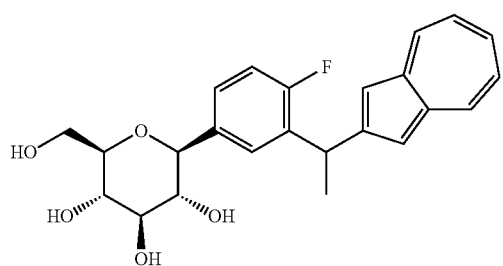
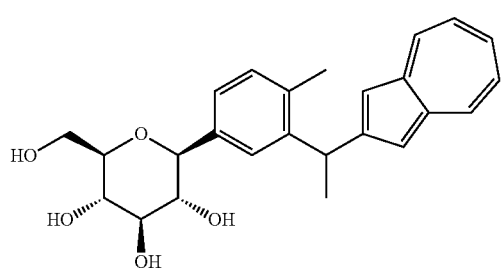
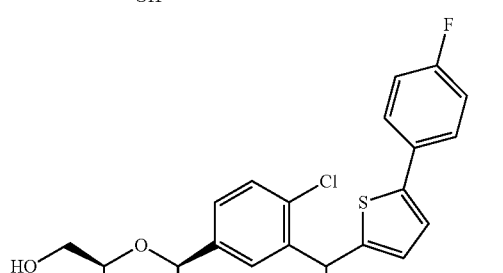
-continued
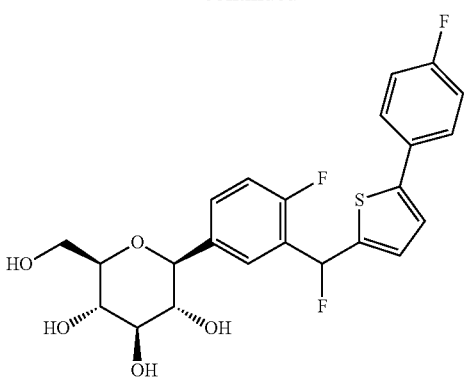 [SMILES: Cc1ccc([C@@H]2O[C@H](CO)[C@@H](O)[C@H](O)[C@H]2O)cc1C(C)c1ccc(-c2ccc(F)cc2)s1]
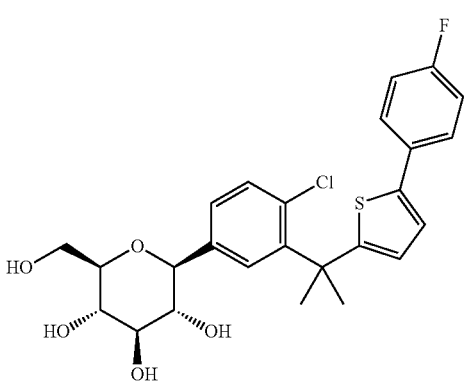
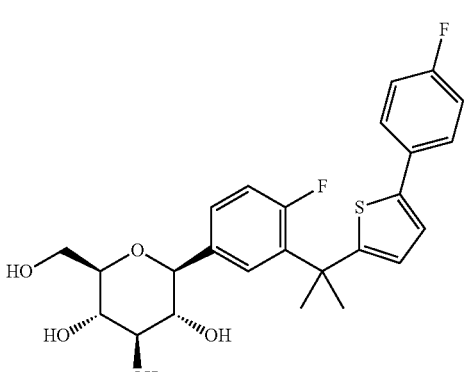
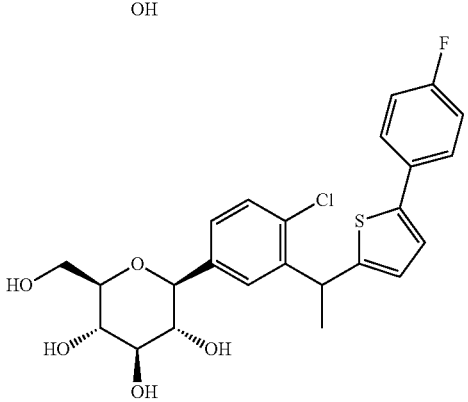

-continued
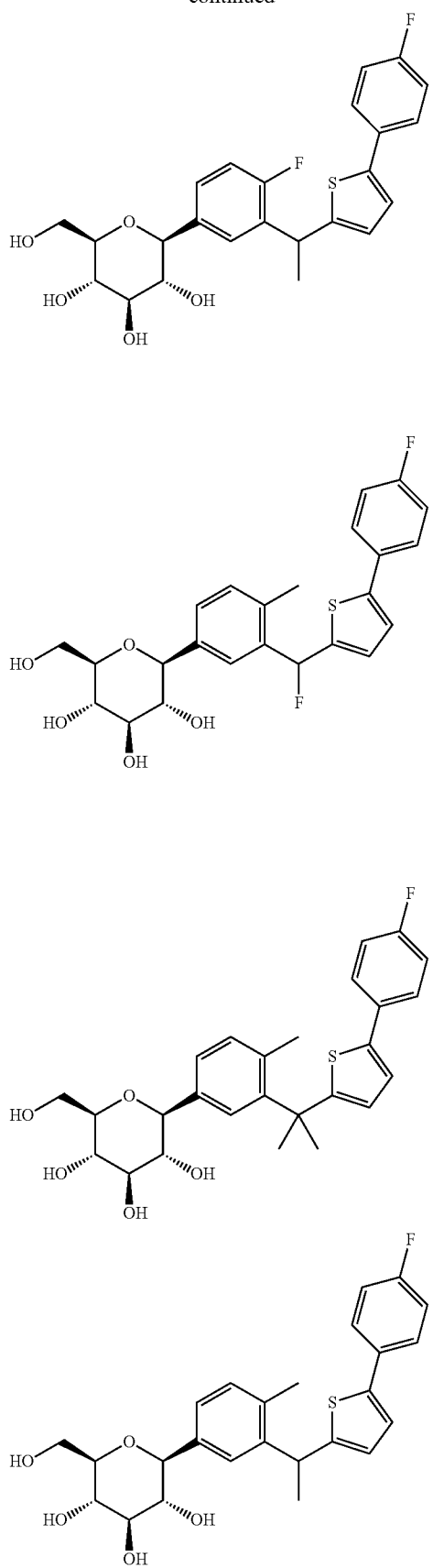
The compound of general formula I of the present invention can be synthesized by the following steps:
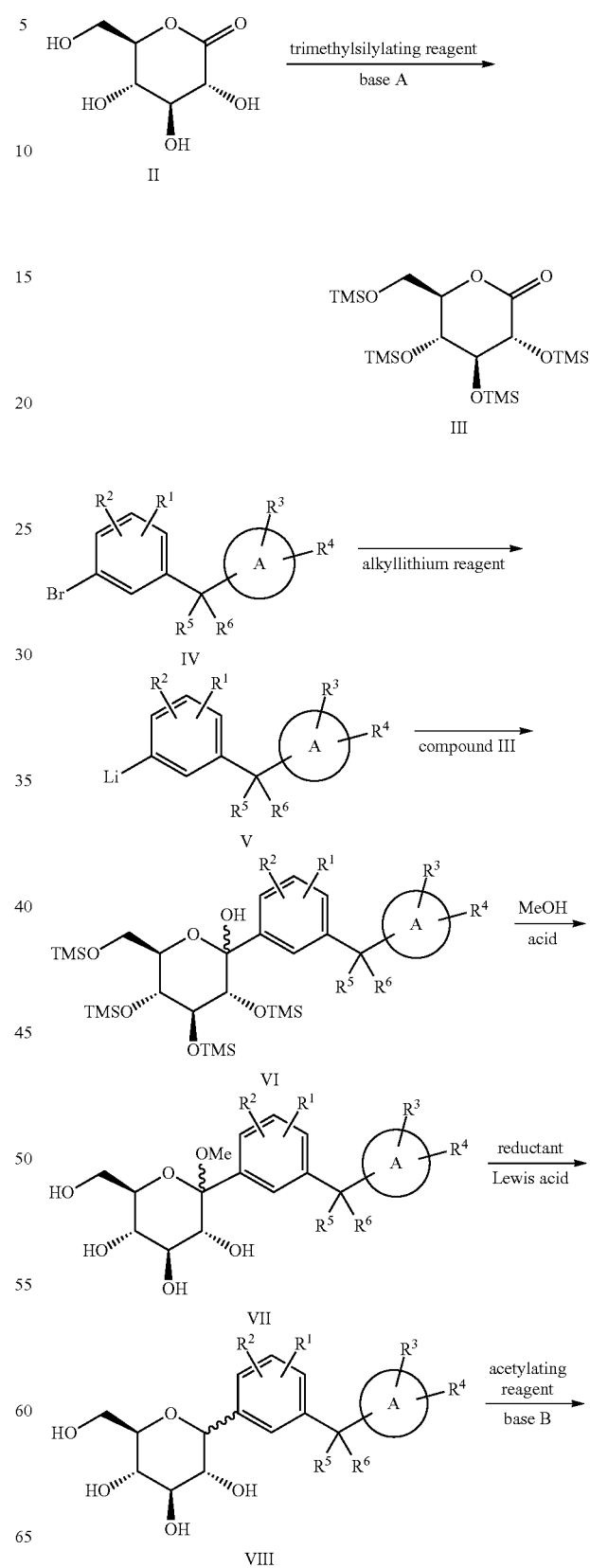

-continued

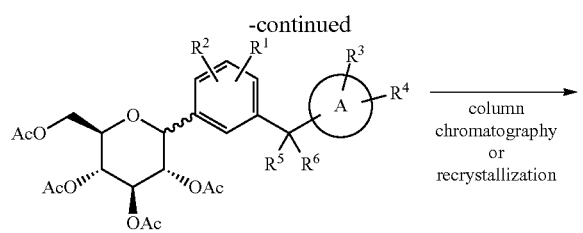

IX

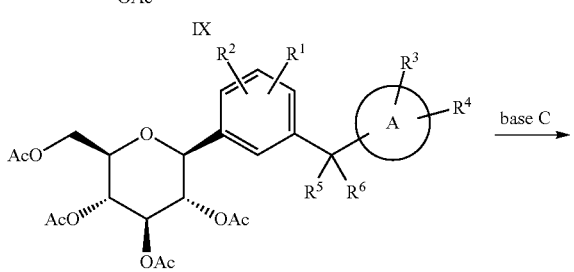

X

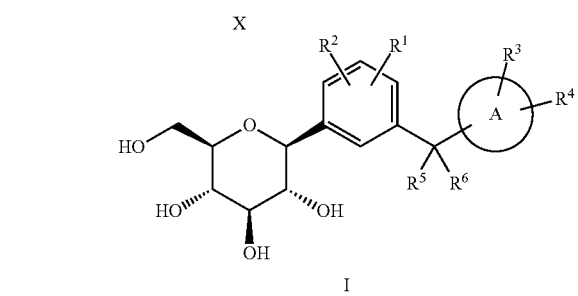

I wherein, the base A can be selected from N-methylmorpholine, triethylamine, pyridine and 4-dimethylaminopyridine, the base B can be selected from anhydrous sodium acetate, pyridine and 4-dimethylaminopyridine, and the base C can be selected from sodium methoxide, NaOH and KOH.

In the above synthesis steps, the trimethylsilylating reagent can be trimethylchlorosilane; the alkyllithium reagent can be n-butyllithium; the acid can be selected from methanesulfonic acid and trifluoromethanesulfonic acid; the Lewis acid can be selected from $BF_3 \cdot Et_2O$, $BF_3 \cdot MeCN$ and trifluoroacetic acid; the reductant can be selected from triethylsilane and triisopropylsilane; and the acetylating reagent can be selected from acetic anhydride and acetyl chloride.

Compound II is treated with trimethylsilylating reagent in the presence of a base to produce compound III. The base is such as N-methyl morpholine, triethylamine, pyridine, 4-dimethylamino-pyridine etc., and the trimethylsilylating reagent is such as trimethylchlorosilane etc.

Compound IV is treated with an alkyllithium reagent such as n-butyllithium to produce compound V, and the compound V, without isolation, reacts with the compound II directly in the reaction mixture to produce compound VI. The compound VI is treated with methanol under the catalysis of an acid such as methanesulfonic acid, trifluoromethanesulfonic acid and p-toluenesulfonic acid etc. to produce compound VII. The compound VII is reduced to compound VIII by a reductant such as triethylsilane, triisopropylsilane etc. in the presence of a Lewis acid such as $BF_3 \cdot Et_2O$, $BF_3 \cdot MeCN$ or trifluoroacetic acid etc. The compound VIII is acetylated to IX with one of acetic anhydride, acetyl chloride etc. in the presence of a base such as anhydrous sodium acetate, pyridine and 4-dimethylamino-pyridine. The compound IX is subjected to column chromatography or recrystallization etc. to produce compound X. The compound X is treated with a base such as sodium methoxide, NaOH, KOH ect. to remove of the acetyl to produce compound I.

In particular, the compound of general formula I of the invention is synthesized by the following steps:

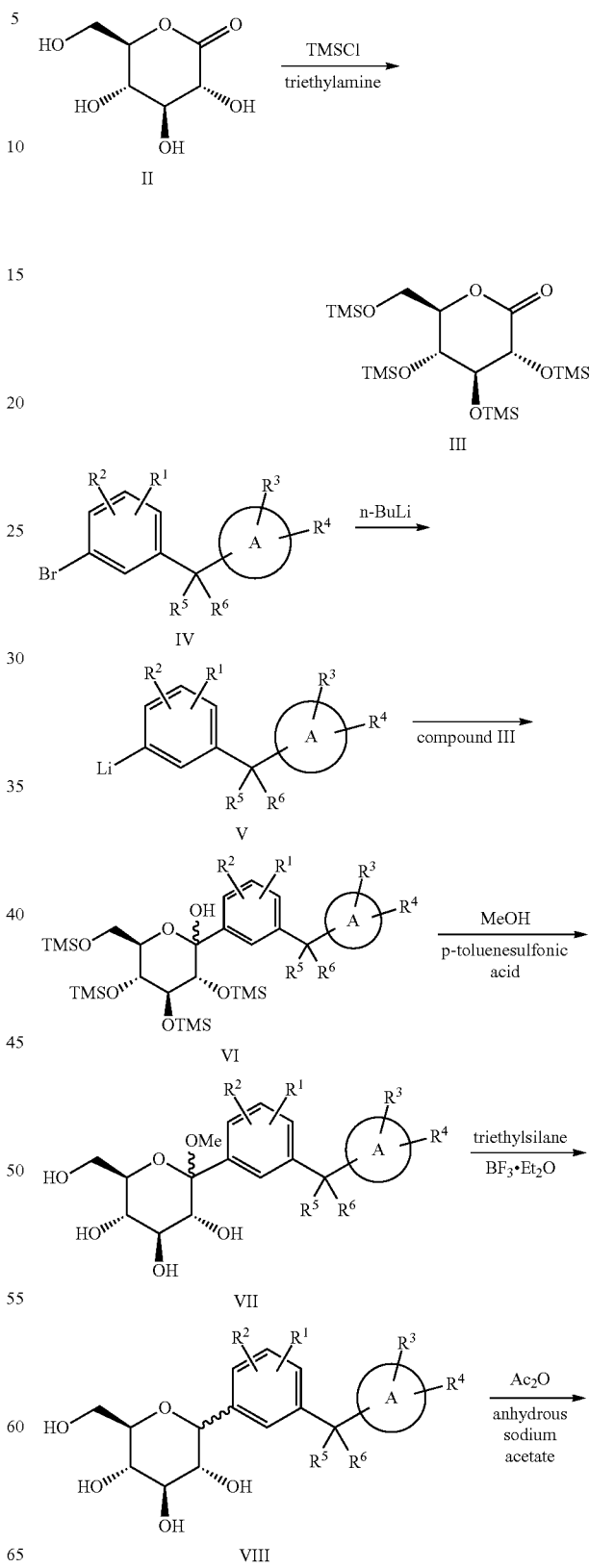

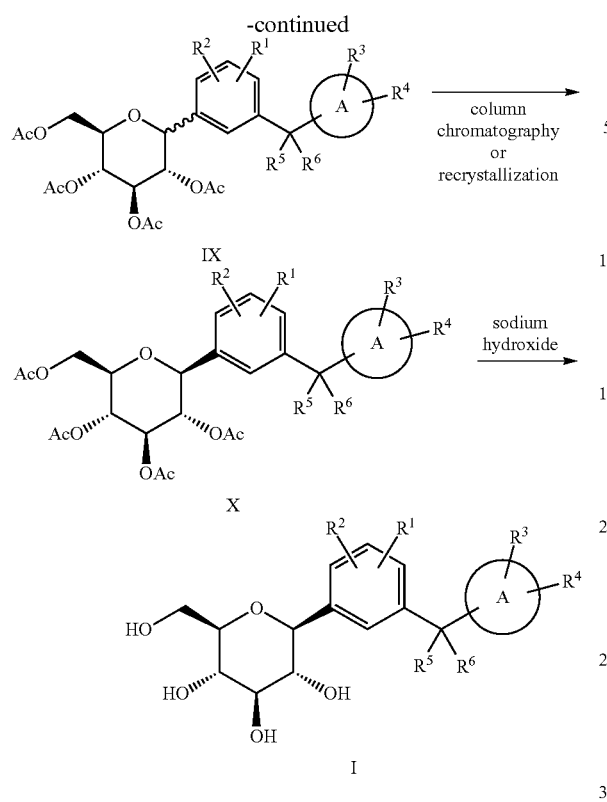

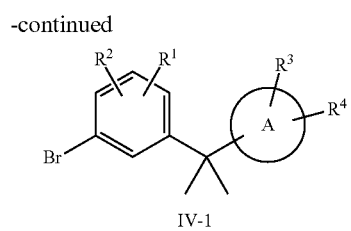

Compound XVIII is treated with a reagent such as MeLi, MeMgI or MeMgBr to produce compound XIX. The compound XIX reacts with compound XII in the presence of an acid such as methanesulfonic acid, trifluoromethanesulfonic acid, p-toluenesulfonic acid or concentrated sulfuric acid to produce compound IV-1.

(2) $R^5$=Me, $R^6$=OMe

In this case, the compound IV can be represented as compound IV-2.

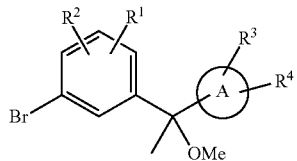

The compound IV can be prepared by the following different routes in accordance with the different selections of $R^5$ and $R^6$.

(1) $R^5$=$R^6$=Me

In this case, the compound IV can be represented as compound IV-1.

Compound IV-2 is synthesized by the following route,

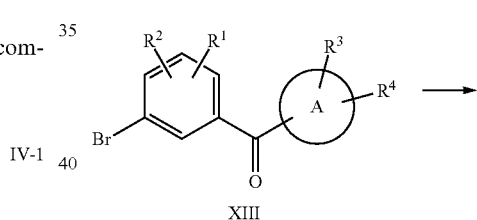

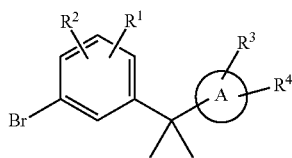

The compound IV-1 is synthesized by the following route,

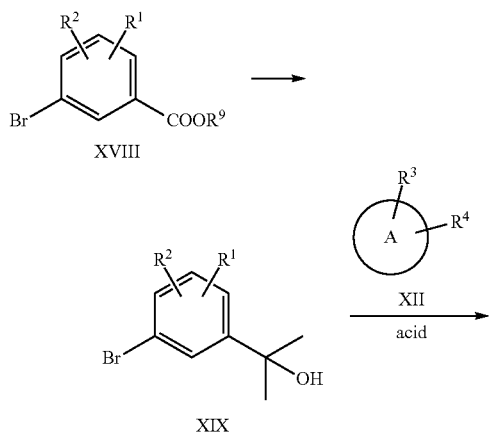

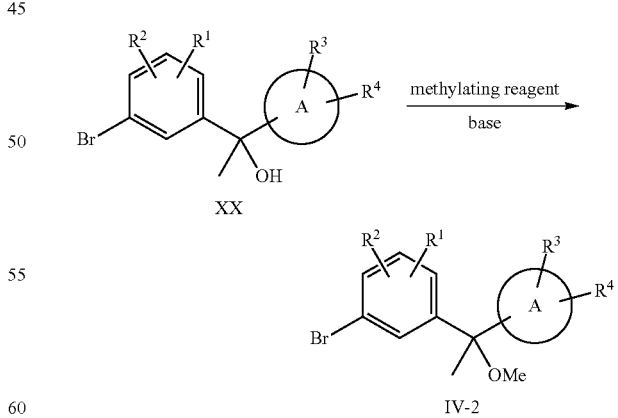

Compound XIII is treated with a reagent such as MeLi, MeMgI or MeMgBr to produce compound XX. The compound XX is treated with methylating reagent such as $Me_2SO_4$ or Met in the presence of a base such as NaH, KH or $NaNH_2$ to produce compound IV-2.

Alternatively, the compound XX in the above route can be synthesized by the following method:

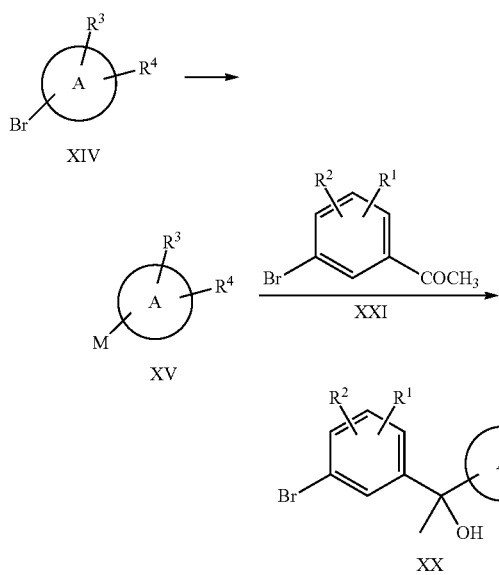

Compound XIV is treated with n-BuLi or metal Mg to produce compound XV. The compound XV reacts with compound XXI to produce compound XX.

(3) $R^5$=Me, $R^6$=H

In this case, the compound IV can be represented as compound IV-3.

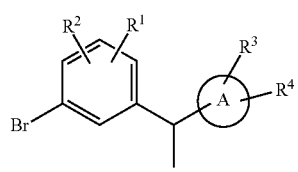
IV-3

Compound IV-3 is synthesized by the following route:

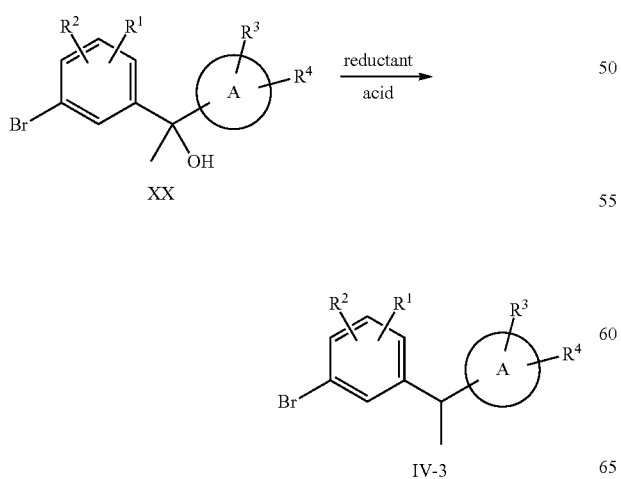

Compound XX is reduced to compound IV-3 with a reductant such as triethylsilane or triisopropylsilane in the presence of an acid such as $BF_3 \cdot Et_2O$ or trifluoroacetic acid.

(4) $R^5$=Me, $R^6$=F

In this case, the compound IV can be represented as compound IV-4.

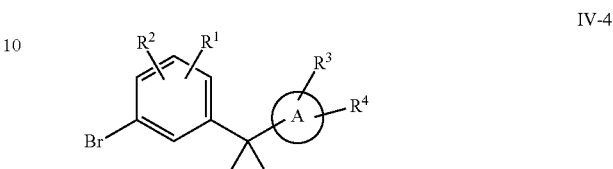
IV-4

The compound IV-4 is synthesized by the following route:

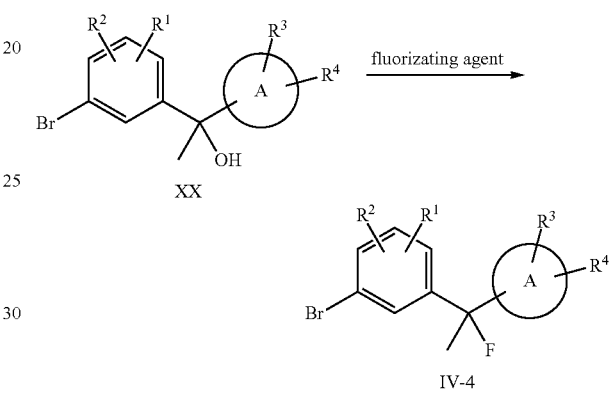
IV-4

Compound XX reacts with a fluorinating agent such as $SF_4$ or $Et_2NSF_3$ to produce compound IV-4.

(5) $R^5$=F, $R^6$=H

In this case, the compound IV can be represented as compound IV-5.

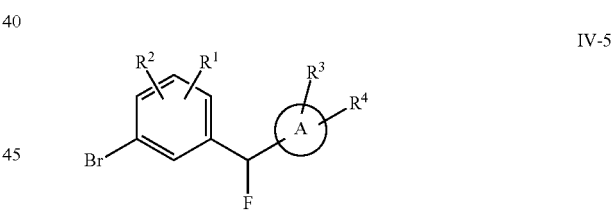
IV-5

The compound IV-5 is synthesized by the following route:

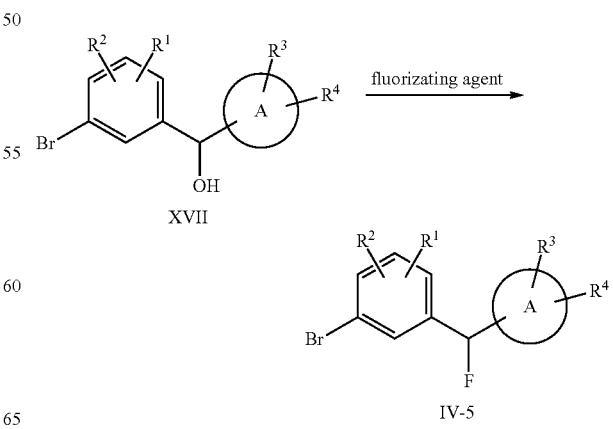
IV-5

Compound XVII reacts with a fluorinating agent such as $SF_4$ or $Et_2NSF_3$ to produce compound IV-5.

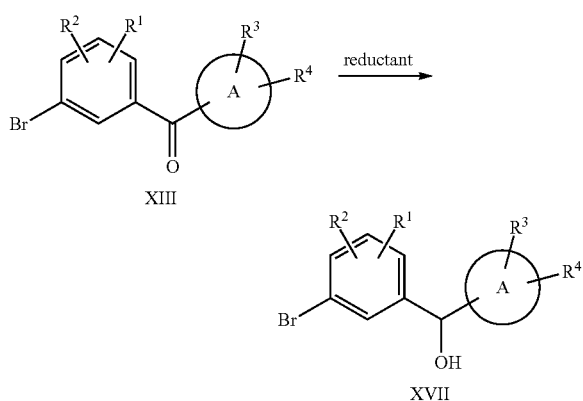

Compound XVII can be produced by reducing compound XIII with a reductant selected from NaBH$_4$, KBH$_4$, LiAlH$_4$ and LiBH$_4$ etc.

(6) R$^5$=OMe, R$^6$=H

In this case, the compound IV can be represented as compound IV-6.

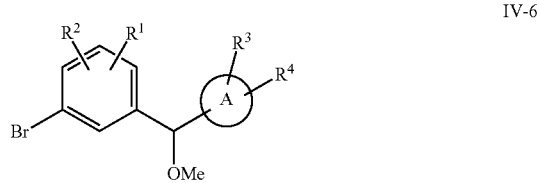

The compound IV-6 is synthesized by the following route:

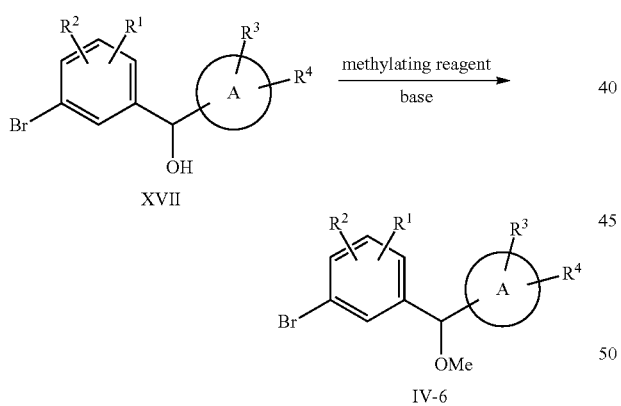

Compound XVII is treated with a methylating reagent such as Me$_2$SO$_4$ or MeI in the presence of a base such as NaH, KH or NaNH$_2$ to produce compound IV-6.

The pharmaceutically acceptable prodrug ester of the compound of general formula I of the invention includes an ester formed from esterification of any one or more hydroxyl groups present in the molecule with an acetyl, a pivaloyl, one of the various phosphoryls, a carbamoyl, an alkoxyformyl and the like.

The compound of general formula I of the invention may be combined with one or more pharmaceutically acceptable carriers, excipients or diluents to prepare a pharmaceutical composition. The pharmaceutical composition may be formulated into a solid oral preparation, a liquid oral preparation, an injectable preparation, etc. The solid oral preparation and liquid oral preparation include a tablet, a dispersible tablet, a sugar coated preparation, a granule, a dry powder, a capsule and a solution. The injectable preparation includes a vial injection, infusion solution and a freeze-dried powder injection etc.

The pharmaceutically acceptable auxiliary material of the composition of the invention is selected from filler, disintegrant, lubricant, glidant, effervescent agent, corrective, preservative, coating material or other excipients.

The filler may include one or more of lactose, sucrose, dextrin, starch, pregelatinized starch, mannitol, sorbitol, calcium hydrophosphate, calcium sulfate, calcium carbonate and microcrystalline cellulose. The adhesive may include one or more of sucrose, starch, povidone, sodium carboxymethylcellulose, hydroxypropylmethylcellulose, hydroxypropylcellulose, methylcellulose, polyethylene glycol, medicinal ethanol and water. The disintegrant may include one or more of starch, crospovidone, croscarmellose sodium, low substituted hydroxypropylcellulose, carboxymethylcellulose sodium and effervescent disintegrants.

The compound of general formula I of the invention is effective in inhibiting SGLT2, and can be used as active ingredient in preparing medicament for treating diabetes. The activity of the compound of general formula I of the invention is confirmed by in a vivo hypoglycemic model.

The compound of general formula I is effective in a significantly wide dosage range. For example, the daily dosage can be 1 mg-1000 mg/person, and can be administrated in a single or multiple dosing. Actual dosage for taking the compound of general formula I can be determined by a doctor in view of related conditions. The conditions include body status of the subject, administration route, age, body weight, personal reaction to medicament, the severity of the symptoms and so on.

EMBODIMENTS OF THE INVENTION

In the following, the present invention is further described in combination with examples. It should be understand that the following examples are intended to illustrate the present invention, but not to limit the invention. Various modifications which may be made by those skilled in the art in light of the teaching of this invention should be included within the protection scope as claimed by the claims of the present application.

Example 1

1-{4-chloro-3-[(4-ethyoxyphenyl)fluoromethyl]phenyl}-1-deoxy-β-D-glucopyranose

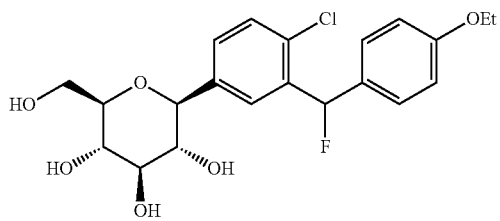

A. (5-bromo-2-chlorophenyl)(4-ethyoxyphenyl)fluoromethane 2.35 g of 5-bromo-2-chlorobenzoic acid, 1.40 g of oxalyl chloride and 5 ml of anhydrous dichloromethane were added into a 100-ml round-bottomed flask, and was magnetically stirred at room temperature. One drop of N,N-dimethylformamide was added thereinto. The mixture was stirred overnight at room temperature, and then the solvent was evaporated on a rotary evaporator. The resulting residue was dissolved in 5 ml of anhydrous dichloromethane and 1.34 g of phenetole was added. The resulting mixture was magnetically stirred in ice water bath, and then 1.73 g of aluminum chloride was slowly added in portions, after which, the reaction mixture was stirred for another 2 hours at room temperature. The reaction mixture was then carefully poured into ice water, stirred, and extracted twice with 100 ml of dichloromethane. The combined extracts were washed by saturated NaCl solution, dried over anhydrous sodium sulfate, and evaporated to dryness on a rotary evaporator. The resulting mixture was purified by column chromatography to give colorless crystals, which were (5-bromo-2-chlorophenyl)(4-ethyoxyphenyl)methanone. ESI-MS, m/z=339.3 ([M($^{79}$Br)+1]), 341.2 ([M($^{81}$Br)+1]).

3.40 g of (5-bromo-2-chlorophenyl)(4-ethyoxyphenyl)methanone prepared as above and 20 ml of anhydrous THF were added into a 100-ml round-bottomed flask, and were stirred in ice water bath. 0.38 G of LiAlH$_4$ was added in portions, after which, the resulting mixture was stirred for another one hour. The reaction mixture was poured carefully into 200 ml of ice water, and then was adjusted to pH 2-3 with concentrated hydrochloric acid. The resulting acidic mixture was extracted twice with 100 ml of dichloromethane. The combined extracts were washed with saturated NaCl solution, dried over anhydrous sodium sulfate, and evaporated to dryness on a rotary evaporator to afford to give a off-white solid, which was (5-bromo-2-chlorophenyl)(4-ethyoxyphenyl)methanol. ESI-MS, m/z=341.1 ([M($^{79}$Br)+1]), 343.3 ([M($^{81}$Br)+1]).

3.07 g of (5-bromo-2-chlorophenyl)(4-ethyoxyphenyl)methanol prepared as above was dissolved in 10 ml of anhydrous dichloromethane, and then 5 ml of (diethylamino)sulfur trifluoride (Et$_2$NSF$_3$) was added. The reaction mixture was stirred overnight at room temperature and poured into 200 ml of ice water, and then was extracted twice with 100 ml of dichloromethane. The combined extracts were washed with saturated NaCl solution, and dried over anhydrous sodium sulfate to give a colorless oily product after removeal of solvents on a rotary evaporator. After being purified by silica column chromatography, a colorless oily product was obtained, which was (5-bromo-2-chlorophenyl)(4-ethyoxyphenyl)fluoromethane. ESI-MS, m/z=343.2 ([M($^{79}$Br)+1]), 345.3 ([M($^{81}$Br)+1]).

B. 1-{4-chloro-3-[(4-ethyoxyphenyl)fluoromethyl]phenyl}-1-deoxy-β-D-glucopyranose 2.72 g of (5-bromo-2-chlorophenyl)(4-ethyoxyphenyl)fluoromethane prepared as above, 10 ml of anhydrous THF and a magnetic stirring bar were added into a 100 ml of round-bottomed flask. The flask was sealed with a rubber septum, and put in an acetone-dry ice system and cooled to −78° C. 8 ml (1.0 M) of n-BuLi was added slowly into the reaction mixture via a syringe while stirring, after which, the mixture was stirred for another one hour in −78° C., and then a solution of 2,3,4,6-tetra-O-trimethylsilyl glucolactone as prepared in example 1 in 10 ml of dried toluene was added slowly into the reaction mixture via a syringe. After addition, the mixture was stirred for another one hour, and then a solution of 1.92 g of methanesulfonic acid dissolved in 10 ml of anhydrous toluene was added dropwise via syringe, and then the mixture was warmed up to room temperature, and stirred overnight at room temperature. The reaction mixture was poured into saturated NaCl solution, and was extracted twice with 100 ml of dichloromethane. The combined extracts were washed by saturated NaCl solution, dried over anhydrous sodium sulfate, and evaporated to dryness on a rotary evaporator to afford to give a colorless oily product, which was methyl 1-{4-chloro-3-[(4-ethyoxyphenyl)fluoromethyl]phenyl}-α/β-D-glucopyranoside, ESI-MS, m/z=457.1 ([M+1]).

3.07 g of the resulting methyl 1-{4-chloro-3-[(4-ethyoxyphenyl)fluoromethyl]phenyl}-α/β-D-glucopyranoside was dissolved in 3 ml of anhydrous dichloromethane, and stirred in ice water bath, and then 2 ml of triethylsilane and 1 ml of boron trifluoride diethyl etherate were added sequentially. The reaction mixture was stirred overnight at room temperature, poured carefully into 100 ml of ice water, adjusted to pH=8 with saturated sodium bicarbonate solution, and extracted twice with 100 ml of dichloromethane. The combined extracts were washed by saturated NaCl solution, dried over anhydrous sodium sulfate, and evaporated to dryness on a rotary evaporator to produce a colorless oily product, which was 1-{4-chloro-3-[(4-ethyoxyphenyl)fluoromethyl]phenyl}-α/β-D-glucopyranose, ESI-MS, m/z=427.4 ([M+1]).

2.57 g of the colorless oily product of the resulting 1-{4-chloro-3-[(4-ethyoxyphenyl) fluoromethyl]phenyl}-α/β-D-glucopyranose was dissolved in 20 ml of acetic anhydride, and 0.5 g of anhydrous sodium acetate was added thereinto. The resulting solution was magnetically stirred and heated to reflux for one hour. After cooling, the mixture was poured into 100 ml of water, stirred overnight at room temperature, and extracted twice with 100 ml of dichloromethane. The combined extracts were washed by saturated NaCl solution, dried over anhydrous sodium sulfate, and evaporated to dryness on a rotary evaporator to afford off-white solid. After being purified by silica column chromatography, colorless crystals were produced, which were 2,3,4,6-tetra-O-acetyl-1-{4-chloro-3-[(4-ethyoxyphenyl)fluoromethyl]phenyl}-1-deoxy-β-D-glucopyranose, ESI-MS, m/z=595.2 ([M+1]).

2.86 g of the above 2,3,4,6-tetra-O-acetyl-1-{4-chloro-3-[(4-ethyoxyphenyl)fluoromethyl]phenyl}-1-deoxy-β-D-glucopyranose was dissolved in 7 ml of anhydrous methanol containing 0.11 g of sodium methoxide, and stirred for 5 hours at room temperature. And then 1 g of dried strongly acidic resin was added, and stirred overnight at room temperature. The resin was removed by filtration, and the resulting filtrate was evaporated to dryness on a rotary evaporator to give a white solid, which was 1-{4-chloro-3-[(4-ethyoxyphenyl)fluoromethyl]phenyl}-1-deoxy-β-D-glucopyranose, ESI-MS, m/z=427.2 ([M+1]).

Examples 2-15

It is understandable that changing $R^1$, $R^2$, $R^3$, $R^4$ and ring A while using the method and process of example 1 can produce the compounds listed in the following table.

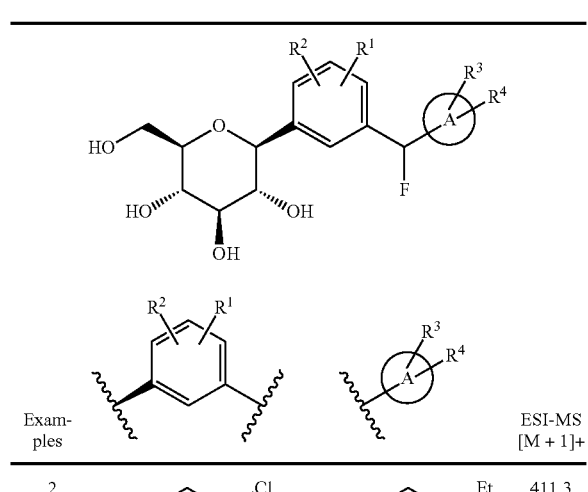
| Examples | R²,R¹ phenyl | A,R³,R⁴ group | ESI-MS [M+1]+ |
|---|---|---|---|
| 2 | 4-Cl | 4-Et phenyl | 411.3 |
| 3 | 4-F | 4-OEt phenyl | 411.3 |
| 4 | 4-F | 4-Et phenyl | 395.3 |
| 5 | 4-Me | 4-OEt phenyl | 407.4 |
| 6 | 4-Me | 4-Et phenyl | 391.1 |
| 7 | 4-Cl | benzothiophen-2-yl | 438.2 |
| 8 | 4-F | benzothiophen-2-yl | 423.4 |
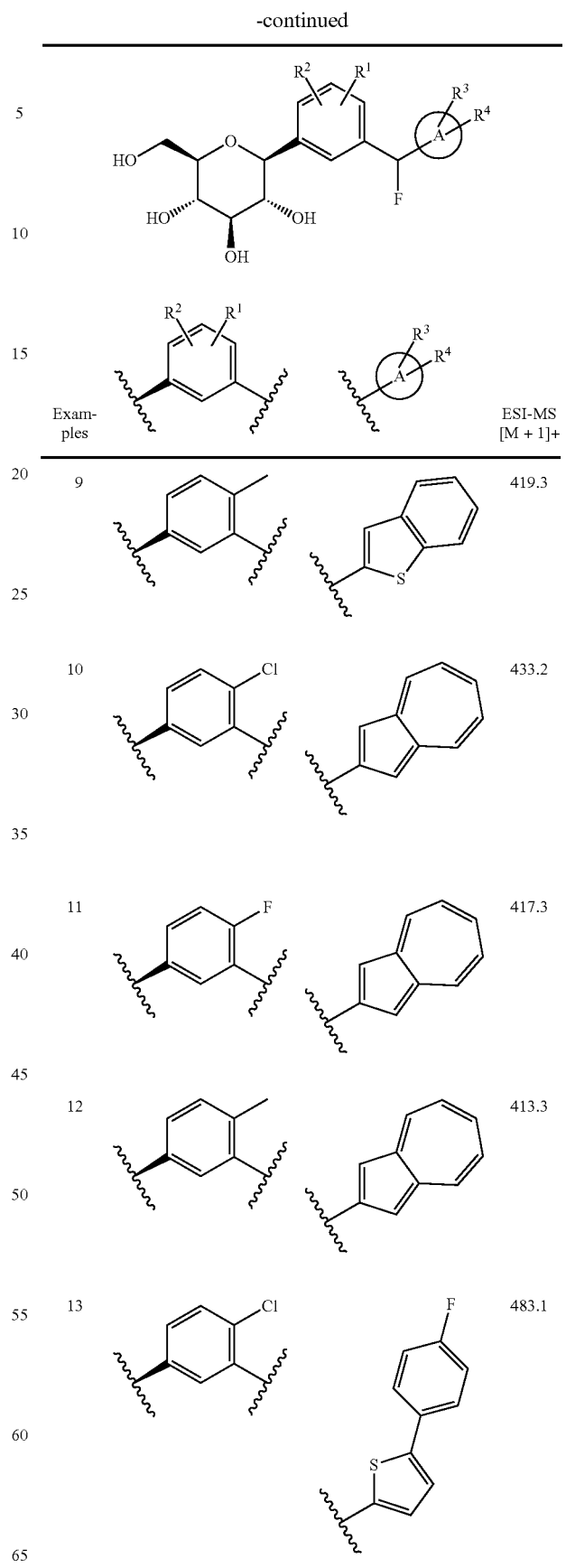
| Examples | R²,R¹ phenyl | A,R³,R⁴ group | ESI-MS [M+1]+ |
|---|---|---|---|
| 9 | 4-Me | benzothiophen-2-yl | 419.3 |
| 10 | 4-Cl | azulen-2-yl | 433.2 |
| 11 | 4-F | azulen-2-yl | 417.3 |
| 12 | 4-Me | azulen-2-yl | 413.3 |
| 13 | 4-Cl | 5-(4-F-phenyl)thiophen-2-yl | 483.1 |

-continued

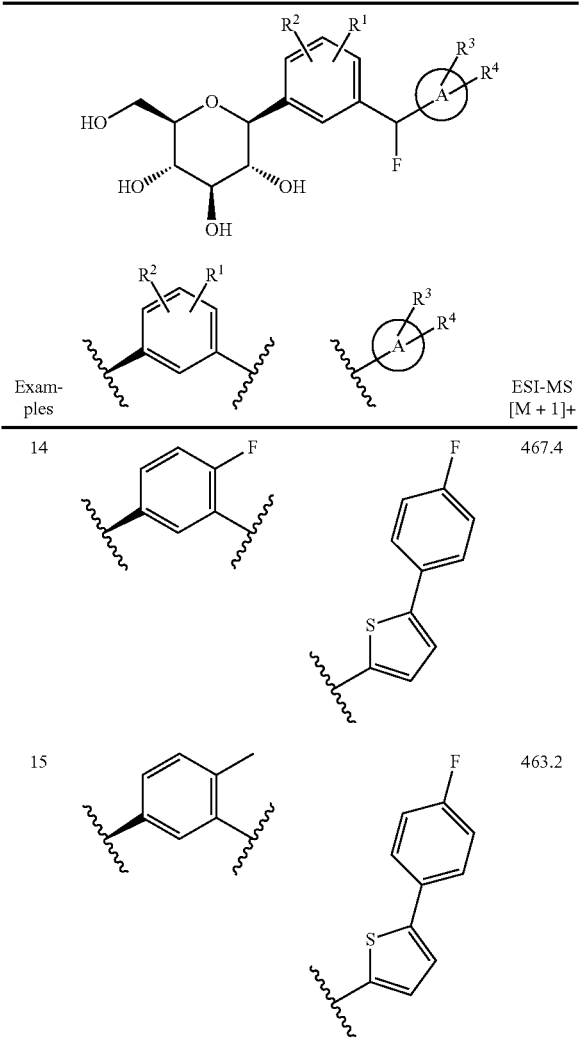

| Examples | R² R¹ | A R³ R⁴ | ESI-MS [M+1]+ |
|---|---|---|---|
| 14 | (4-F, 2-) phenyl | 4-F-phenyl-thiophene | 467.4 |
| 15 | (4-methyl, 2-) phenyl | 4-F-phenyl-thiophene | 463.2 |

Example 16

1-{4-chloro-3-[(dimethyl)(4-ethyoxyphenyl)methyl]phenyl}-1-deoxy-β-D-glucopyranose

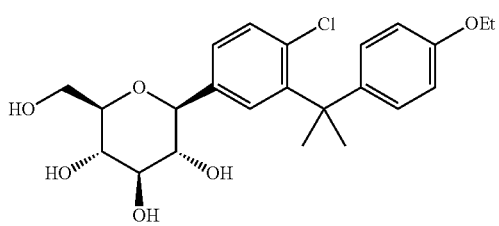 [SMILES: CCOc1ccc(C(C)(C)c2cc([C@@H]3O[C@H](CO)[C@@H](O)[C@H](O)[C@H]3O)ccc2Cl)cc1]

A. (5-bromo-2-chlorophenyl)(4-ethyoxyphenyl)(dimethyl)methane 2.64 g of ethyl 5-bromo-2-chlorobenzoate and 10 ml of anhydrous THF were added into a 100-ml round-bottomed flask, and the resulting solution was cooled in ice water bath and magnetically stirred, and then 25 ml (1.0 M) of methyl iodine magnesium in THF was added using a pressure-equalizing funnel. After addition, the reaction mixture was stirred for one hour at room temperature, poured carefully into 200 ml of ice water, and adjusted to pH=3-4 with concentrated hydrochloric acid. The resulting acidic mixture was extracted twice with 100 ml of dichloromethane. The combined extracts were washed with saturated NaCl solution, dried over anhydrous sodium sulfate, and evaporated to dryness on a rotary evaporator to give a colorless oily product, which was (5-bromo-2-chlorophenyl)dimethylmethanol. $^1$H NMR (DMSO-$d_6$, 400 MHz), δ 7.95 (d, 1H, J=2.8 Hz), 7.44 (dd, 1H, J=2.6 Hz and 8.6 Hz), 7.33 (d, 1H, J=8.0 Hz), 5.46 (s, 1H), 1.56 (s, 6H); ESI-MS, m/z=249.2 ([M($^{79}$Br)+1]), 251.3 ([M($^{81}$Br)+1]).

2.35 g of (5-bromo-2-chlorophenyl)dimethyl methanol described above and 2.44 g (20 mmol) of phenetole were added into a 25-ml round-bottomed flask, and magnetically stirred, and then 4.11 g of anhydrous aluminum chloride was added. The reaction mixture was stirred overnight at 20° C. and poured carefully into 200 ml of ice water. The resulting acidic mixture was extracted twice with 100 ml of dichloromethane. The combined exacts were washed with saturated NaCl solution, dried over anhydrous sodium sulfate, and evaporated to dryness on a rotary evaporator to furnish a colorless oily product, which was 2.69 g of (5-bromo-2-chlorophenyl)(4-ethyoxyphenyl)(dimethyl)methane. The yield was 81%. $^1$H NMR (DMSO-$d_6$, 400 MHz), δ 7.76 (d, 1H, J=2.4 Hz), 7.47 (dd, 1H, J=2.4 Hz and 8.4 Hz), 7.25 (d, 1H, J=8.4 Hz), 6.96 (d, 2H, J=8.8 Hz), 6.78 (d, 2H, J=9.2 Hz), 3.96 (q, 2H, J=7.1 Hz), 1.64 (s, 6H), 1.29 (t, 3H, J=7.0 Hz); ESI-MS, m/z=353.4 ([M($^{79}$Br)+1]), 355.2 ([M($^{81}$Br)+1]).

B. 1-{4-chloro-3-[(dimethyl)(4-ethyoxyphenyl)methyl]phenyl}-1-deoxy-β-D-glucopyranose 2.69 g of (5-bromo-2-chlorophenyl)(4-ethyoxyphenyl)dimethylmethane prepared as above, 10 ml of anhydrous THF and a magnetic stirring bar were added into a 100-ml round-bottomed flask. The flask was sealed with a rubber septum, put in acetone-dry ice system, and cooled to −78° C. 8 ml (1.0 M) n-BuLi was added slowly into the reaction mixture via a syringe while stirring, after which, the mixture was stirred for another one hour at −78° C., and then a solution of 2,3,4,6-tetra-O-trimethylsilylglucolactone as prepared in example 1 in 10 ml of anhydrous toluene was added slowly into the reaction mixture via a syringe. After addition, the mixture was stirred for another one hour, and then a solution of 1.92 g of methanesulfonic acid in 10 ml of anhydrous methanol was added via a syringe, and then the mixture was warmed up to room temperature, and stirred overnight at room temperature. The reaction mixture was poured into a saturated NaCl solution, and was extracted twice with 100 ml of dichloromethane. The combined extracts were washed by saturated NaCl solution, dried over anhydrous sodium sulfate, and evaporated to dryness on a rotary evaporator to give a colorless oily product, which was 1-{4-chloro-3-[(dimethyl)(4-ethyoxyphenyl)methyl]phenyl}-α/β-D-methyl glucopyranoside, ESI-MS, m/z=467.1 ([M+1]).

3.09 g of the resulting methyl 1-{4-chloro-3-[(dimethyl)(4-ethyoxyphenyl)methyl]phenyl}-α/β-D-glucopyranoside was dissolved in 3 ml of anhydrous dichloromethane, and stirred in ice water bath, and then 2 ml of triethylsilane and 1 ml of boron trifluoride diethyl etherate were added sequentially. The resulting reaction mixture was stirred overnight at room temperature, poured carefully into 100 ml of ice water, adjusted to pH=8 with a saturated sodium bicarbonate solution, and then extracted twice with 100 ml of dichloromethane. The combined extracts were washed by saturated NaCl solution, dried over anhydrous sodium sulfate, and evaporated to dryness on a rotary evaporator to yield a colorless oily product, which was 1-{4-chloro-3-[(dimethyl)(4-ethyoxyphenyl)methyl]phenyl}-α/β-D-glucopyranose, ESI-MS, m/z=437.2 ([M+1]).

2.62 g of the resulting colorless oily product of 1-{4-chloro-3-[(dimethyl)(4-ethyoxyphenyl)methyl]phenyl}-α/β-D-glucopyranose was dissolved in 20 ml of acetic anhydride, and 0.5 g of anhydrous sodium acetate was added. The resulting solution was magnetically stirred and heated to reflux for one hour. After cooling, the mixture was poured into 100 ml of water, stirred overnight at room temperature, and extracted twice with 100 ml of dichloromethane. The combined extracts were washed by saturated NaCl solution, dried over anhydrous sodium sulfate, and evaporated to dryness on a rotary evaporator to give an off-white solid. After being purified by silica column chromatography, colorless crystals were produced, which was 2,3,4,6-tetra-O-acetyl-1-{4-chloro-3-[(4-ethyoxyphenyl)methyl]phenyl}-1-deoxy-β-D-glucopyranose. $^1$H NMR (DMSO-$d_6$, 400 MHz), δ 7.58 (s, 1H), 7.27 (s, 2H), 6.90 (d, 2H, J=8.8 Hz), 6.76 (d, 2H, J=8.8 Hz), 5.39 (t, 1H, J=9.6 Hz), 5.13 (t, 1H, J=9.6 Hz), 5.05 (t, 1H, J=9.6 Hz), 4.78 (d, 1H, J=9.6 Hz), 4.14-4.15 (m, 2H), 4.06-4.11 (m, 1H), 3.95 (q, 2H, J=6.9 Hz), 2.02 (s, 3H), 2.01 (s, 3H), 1.94 (s, 3H), 1.82 (s, 3H), 1.64 (s, 6H), 1.28 (t, 3H, J=7.0 Hz); ESI-MS, m/z=605.3 ([M+1]).

3.27 g of 2,3,4,6-tetra-O-acetyl-1-{4-chloro-3-[(4-ethyoxyphenyl)methyl]phenyl}-1-deoxy-β-D-glucopyranose prepared as above was dissolved in 7 ml of anhydrous methanol containing 0.11 g of sodium methoxide, and stirred for 5 hours at room temperature, and then 1 g of dried strongly acidic resin was added, and stirred overnight at room temperature. The resin was removed by filtration, and the resulting filtrate was evaporated to dryness on a rotary evaporator to yield a white solid, which was 1-{4-chloro-3-[(dimethyl)(4-ethyoxyphenyl)methyl]phenyl}-1-deoxy-β-D-glucopyranose. $^1$H NMR (DMSO-$d_6$, 400 MHz), 87.62 (s, 1H), 7.23 (s, 2H), 6.97 (d, 2H, J=8.8 Hz), 6.76 (d, 2H, J=8.8 Hz), 4.93-4.95 (m, 2H), 4.87 (d, 1H, J=5.6 Hz), 4.46 (t, 1H, J=5.8 Hz), 4.09 (d, 1H, J=9.6 Hz), 3.95 (q, 2H, J=6.9 Hz), 3.71-3.75 (m, 1H), 3.44-3.50 (m, 1H), 3.24-3.30 (m, 2H), 3.15-3.22 (m, 2H), 1.653 (s, 3H), 1.645 (s, 3H), 1.29 (t, 3H, J=7.0 Hz); ESI-MS, m/z=437.4 ([M+1]).

Example 17-35

It is understandable that changing $R^1$, $R^2$, $R^3$, $R^4$ and ring A while using the method and process of example 16 can produce the compounds listed in the following table.

| Examples | $R^1$/$R^2$ substituted phenyl | Ring A with $R^3$/$R^4$ | ESI-MS [M+1]$^+$ |
|---|---|---|---|
| 17 | 4-Cl | 4-Et | 421.1 |
| 18 | 4-F | 4-OEt | 421.2 |
| 19 | 4-F | 4-Et | 405.2 |
| 20 | 4-Me | 4-OEt | 417.3 |
| 21 | 4-Me | 4-Et | 401.3 |
| 22 | H | 4-OEt | 403.1 |
| 23 | 4-OMe | 4-OEt | 433.3 |

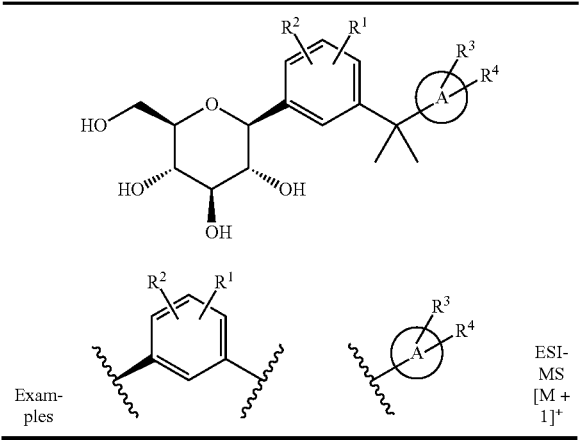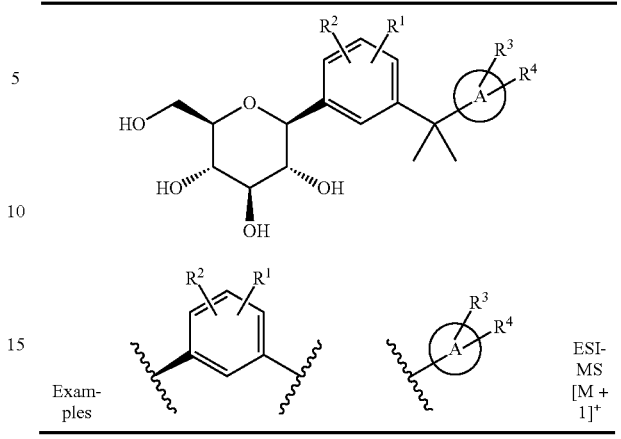

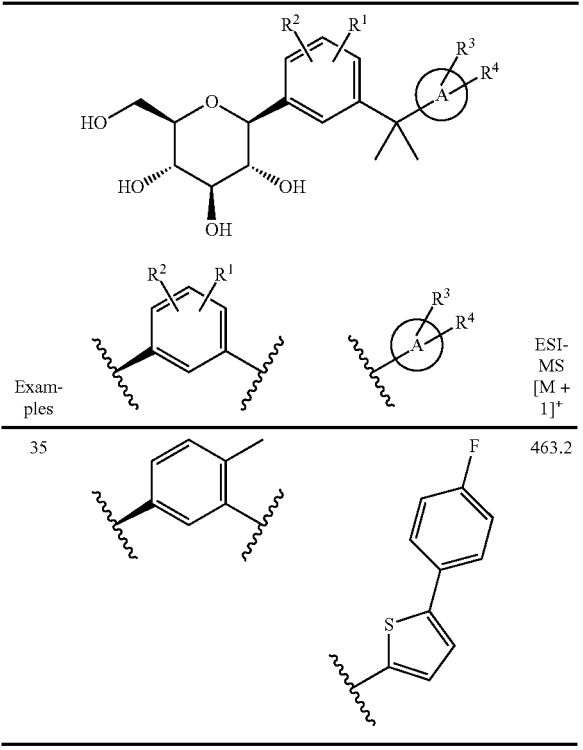

| Examples | <br>(R²/R¹ phenyl linker) | <br>(A/R³/R⁴ group) | ESI-MS [M+1]⁺ |
|---|---|---|---|
| 35 | 4-methyl-phenyl linker | 4-fluorophenyl-thiophene | 463.2 |

Example 36

1-{4-chloro-3-[1-(4-ethyoxyphenyl)ethyl]phenyl}-1-deoxy-β-D-glucopyranose

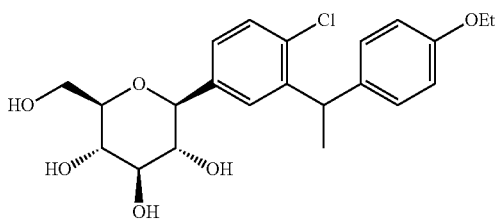 [SMILES: CCOc1ccc(C(C)c2cc([C@@H]3O[C@H](CO)[C@@H](O)[C@H](O)[C@H]3O)ccc2Cl)cc1]

A. 1-(5-bromo-2-chlorophenyl)-1-(4-ethyoxyphenyl)ethane 3.40 g of (5-bromo-2-chlorophenyl)-1-(4-ethyoxyphenyl) ketone and 10 ml of anhydrous THF were added to a 100-ml round-bottomed flask, and the resulting solution was cooled in ice-water bath and magnetically stirred, and then 10 ml (1.0 M) of methyl iodine magnesium in THF was added with a pressure-equalizing funnel. After addition, the reaction mixture was stirred for one hour at room temperature, poured carefully into 200 ml of ice water, and adjusted to pH=3-4 with concentrated hydrochloric acid. The resulting acidic mixture was extracted twice with 100 ml of dichloromethane. The combined extracts were washed with saturated NaCl solution, dried over anhydrous sodium sulfate, and evaporated to dryness on a rotary evaporator to produce a colorless oily product, which was 1-(5-bromo-2-chlorophenyl)-1-(4-ethyoxyphenyl)ethanol. ESI-MS, m/z=355.2 ([M($^{79}$Br)+1]), 357.2 ([M($^{81}$Br)+1]).

3.20 g of the 1-(5-bromo-2-chlorophenyl)-1-(4-ethyoxyphenyl)ethanol described as above was added into a 25-ml round-bottomed flask, dissolved in 3 ml of anhydrous dichloromethane and magnetically stirred. Then 2 ml of triethylsilane and 1 ml of boron trifluoride diethyl etherate were added sequentially. The reaction mixture was stirred overnight at room temperature and then poured carefully into 200 ml of ice water. The resulting acidic mixture was extracted twice with 100 ml of dichloromethane. The combined extracts were washed by saturated NaCl solution, dried over anhydrous sodium sulfate, and evaporated to dryness on a rotary evaporator to produce a colorless oily product, which is 1-(5-bromo-2-chlorophenyl)-1-(4-ethyoxyphenyl)ethane. ESI-MS, m/z=339.2 ([M($^{79}$Br)+1]), 341.3 ([M($^{81}$Br)+1]).

B. 1-{4-chloro-3-[1-(4-ethyoxyphenyl)ethyl]phenyl}-1-deoxy-β-D-glucopyranose 2.45 g of 1-(5-bromo-2-chlorophenyl)-1-(4-ethyoxyphenyl)ethane prepared as above, 10 ml of anhydrous THF and a magnetic stirring bar were added into a 100-ml round-bottomed flask. The flask was sealed with a rubber septum, and put in acetone-dry ice system and cooled to −78° C. 8 ml (1.0 M) of n-BuLi was added slowly into the reaction container via a syringe while stirring, after which, the reaction was stirred for another one hour in −78° C., and then a solution of 2,3,4,6-tetra-O-trimethylsilylglucolactone as prepared in example 1 in 10 ml of anhydrous toluene was added slowly into the reaction mixture via syringe. After addition, the mixture was stirred for another one hour, and a solution of 1.92 g of methanesulfonic acid in 10 ml of anhydrous methanol was added via syringe, and then the mixture was warmed up to room temperature, and stirred overnight at room temperature. The reaction mixture was poured into a saturated NaCl solution, and was extracted twice with 100 ml of dichloromethane. The combined extracts were washed with saturated NaCl solution, dried over anhydrous sodium sulfate, and evaporated to dryness on a rotary evaporator to give a colorless oily product, which was methyl 1-{4-chloro-3-[1-(4-ethyoxyphenyl)ethyl]phenyl}-α/β-D-glucopyranoside, ESI-MS, m/z=453.4 ([M+1]).

2.77 g of the resulting oily product of methyl 1-{4-chloro-3-[1-(4-ethyoxyphenyl)ethyl]phenyl}-α/β-D-glucopyranoside was dissolved in 3 ml of anhydrous dichloromethane, and stirred in ice water bath, and then 2 ml of triethylsilane and 1 ml of boron trifluoride diethyl etherate were added sequentially. The reaction mixture was stirred overnight at room temperature, poured carefully into 100 ml of ice water, adjusted to pH=8 with saturated sodium bicarbonate solution, and extracted with twice with 100 ml of dichloromethane. The combined extracts were washed with saturated NaCl solution, dried over anhydrous sodium sulfate, and evaporated to dryness on a rotary evaporator to afford a colorless oily product, which was 1-{4-chloro-3-[1-(4-ethyoxyphenyl) ethyl]phenyl}-α/β-D-glucopyranose, ESI-MS, m/z=423.2 ([M+1]).

2.32 g of the resulting colorless oily product of 1-{4-chloro-3-[1-(4-ethyoxyphenyl)ethyl]phenyl}-α/β-D-glucopyranose was dissolved in 20 ml of acetic anhydride, and 0.5 g of anhydrous sodium acetate was added. The resulting solution was magnetically stirred and heated to reflux for one hour. After cooling, the mixture was poured into 100 ml of water, stirred overnight at room temperature, and then extracted twice with 100 ml dichloromethane. The combined extracts were washed with saturated NaCl solution, dried over anhydrous sodium sulfate, and evaporated to dryness on a rotary evaporator to afford an off-white solid. After being purified by silica column chromatography, colorless crystals were produced, which were 2,3,4,6-tetra-O-acetyl-1-{4-chloro-3-[1-(4-ethyoxyphenyl)ethyl]phenyl}-1-deoxy-β-D-glucopyranose. ESI-MS, m/z=591.4 ([M+1]).

3.12 g of the above 2,3,4,6-tetra-O-acetyl-1-{4-chloro-3-[1-(4-ethyoxyphenyl)ethyl]phenyl}-1-deoxy-β-D-glucopyranose was dissolved in 7 ml of anhydrous methanol containing 0.11 g of sodium methoxide, and stirred for 5 hours at room temperature, and then 1 g of dried strongly acidic resin was added, and stirred overnight at room temperature. The resin was removed by filtration, and the resulting filtrate was evaporated to dryness on a rotary evaporator to afford a white solid, which was 1-{4-chloro-3-[1-(4-ethyoxyphenyl)ethyl]phenyl}-1-deoxy-β-D-glucopyranose, ESI-MS, m/z=423.2 ([M+1]); $^1$H NMR (DMSO-$d_6$, 400 MHz), δ 7.30-7.38 (m, 2H), 7.20-7.22 (d, 1H, J=8.4 Hz), 7.08-7.11 (m, 2H), 6.79-6.82 (m, 2H), 4.43-4.48 (m, 1H), 3.93-4.03 (m, 3H), 3.68-3.70 (d, 1H, J=11.6 Hz), 3.42-3.46 (m, 1H), 3.07-3.29 (m, 4H), 1.52-1.53 (d, 3H, J=6.8 Hz), 1.27-1.30 (t, 3H, J=7.0 Hz).

Example 37-50

It is understandable that changing $R^1$, $R^2$, $R^3$, $R^4$ and ring A while using the method and process of example 36 can produce the compounds listed in the following table.

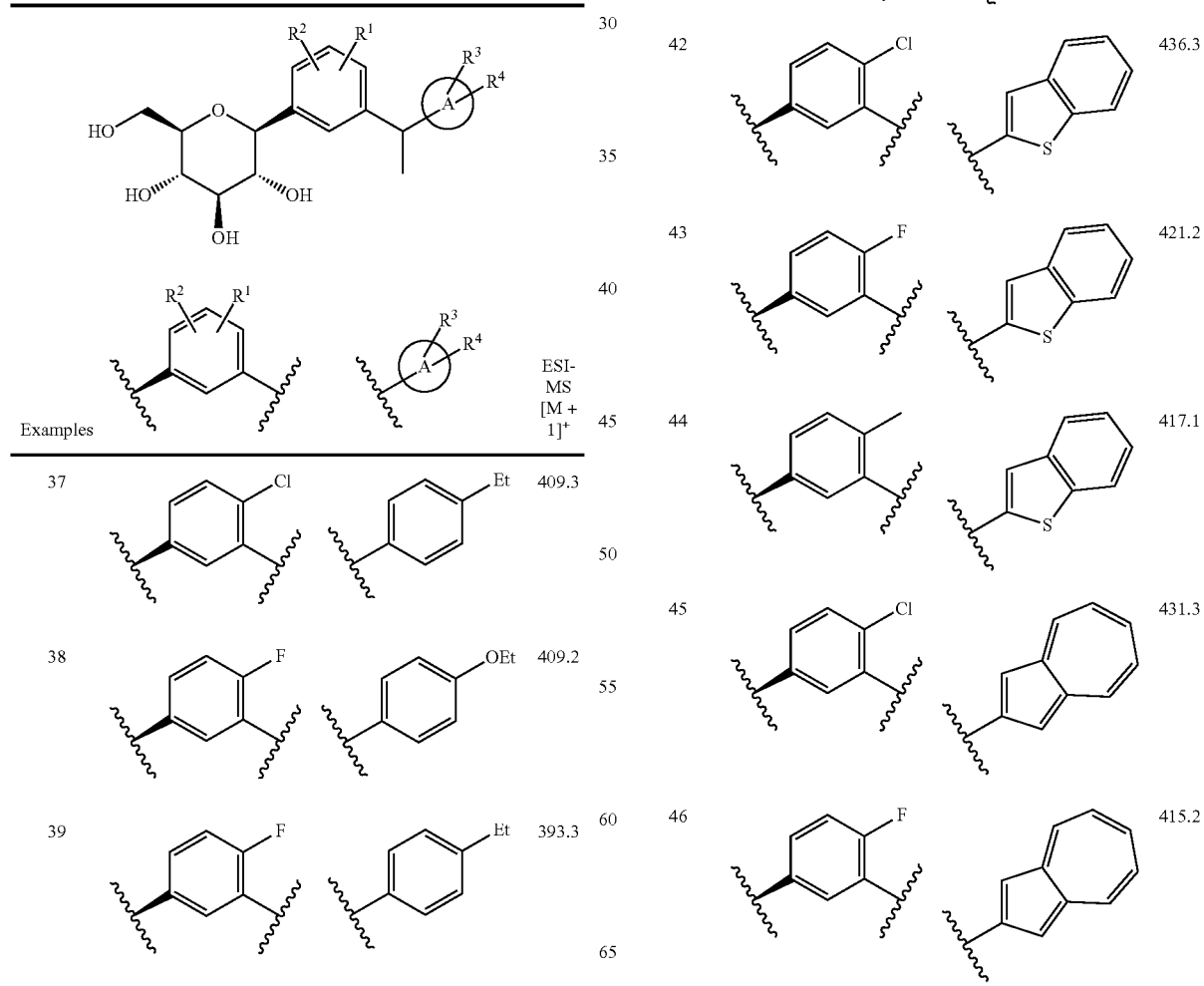

-continued

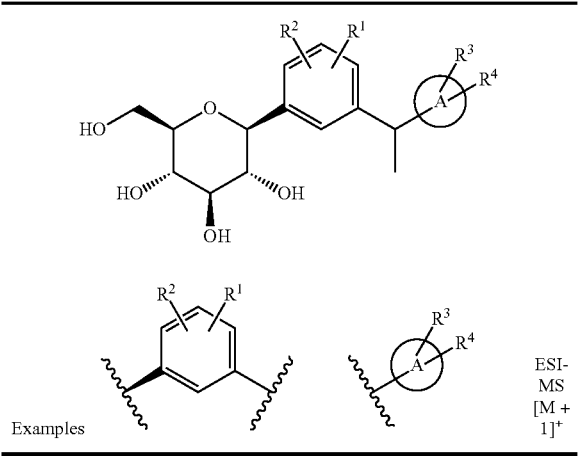

| Examples | R²/R¹ ring | A/R³/R⁴ ring | ESI-MS [M+1]⁺ |
|---|---|---|---|
| 47 | 4-methyl, 3- | azulene (2-yl) | 411.3 |
| 48 | 4-Cl | 5-(4-F-phenyl)thiophen-2-yl | 471.3 |
| 49 | 4-F | 5-(4-F-phenyl)thiophen-2-yl | 455.2 |
| 50 | 4-methyl | 5-(4-F-phenyl)thiophen-2-yl | 451.3 |

Example 51

1-{4-chloro-3-[1-(4-ethyoxyphenyl)-1-methoxy-ethyl]phenyl}-1-deoxy-β-D-glucopyranose A. 1-(5-bromo-2-chlorophenyl)-1-(4-ethyoxyphenyl)-1-methoxyethane 3.40 g of (5-bromo-2-chlorophenyl)(4-ethyoxyphenyl)(methyl)methanol and 10 ml of anhydrous THF were added into a 100-ml round-bottomed flask, and the resulting solution was cooled in ice-water bath and magnetically stirred. 0.40 g (60%) of solid NaH was added in portions, after which, the resulting mixture was stirred for another one hour, and then 1.70 g of dried MeI was added. The reaction mixture was stirred overnight at room temperature and poured carefully into 200 ml of ice water, and then concentrated hydrochloric acid was used to adjust pH to 2-3. The resulting acid mixture was extracted twice with 100 ml of dichloromethane. The combined extracts were washed with saturated NaCl solution, dried over anhydrous sodium sulfate, and evaporated to dryness on a rotary evaporator to afford a colorless oily product, which was 1-(5-bromo-2-chlorophenyl)-1-(4-ethyoxyphenyl)-1-methoxyethane. ESI-MS, m/z=369.2 ([M($^{79}$Br)+1]), 371.4 ([M($^{81}$Br)+1]).

B. 1-{4-chloro-3-[1-(4-ethyoxy-phenyl)-1-methoxy-ethyl]phenyl}-1-deoxy-β-D-glucopyranose 3.40 g of 1-(5-bromo-2-chlorophenyl)-1-(4-ethyoxyphenyl)-1-methoxyethane prepared as above, 10 ml of anhydrous THF and a magnetic stirring bar were added into a 100-ml round-bottomed flask. The flask was sealed with a rubber septum, put in acetone-dry ice system and cooled to −78° C. 10 ml of (1.0 M) n-BuLi was added slowly into the reaction mixture via syringe while stirring, after which, the mixture was stirred for another one hour at −78° C., and then a solution of 2,3,4,6-tetra-O-trimethylsilyl glucolactone as prepared in example 1 in 10 ml of anhydrous toluene was added slowly into the reaction mixture via a syringe. After addition, the mixture was stirred for another one hour, and a solution of 1.92 g of methanesulfonic acid in 10 ml of anhydrous methanol was added via a syringe, and then the mixture was warmed up to room temperature, and stirred overnight at room temperature. The reaction mixture was poured into a saturated NaCl solution, and was extracted twice with 100 ml of dichloromethane. The combined extracts were washed by saturated NaCl solution, dried over anhydrous sodium sulfate, and evaporated to dryness on a rotary evaporator to afford a colorless oily product, which was methyl 1-{4-chloro-3-[1-(4-ethyoxyphenyl)-1-methoxyethyl]phenyl}-α/β-D-glucopyranoside, ESI-MS, m/z=483.4 ([M+1]).

3.69 g of the resulting methyl 1-{4-chloro-3-[1-(4-ethyoxy-phenyl)-1-methoxy-ethyl]phenyl}-α/β-D-glucopyranoside was dissolved in 3 ml of anhydrous dichloromethane, and stirred in ice water bath, and then 2 ml of triethylsilane and 1 ml of boron trifluoride diethyl etherate were added sequentially. The reaction mixture was stirred overnight at room temperature, poured carefully into 100 ml of ice water, adjusted to pH=8 with saturated sodium bicarbonate solution, and extracted twice with 100 ml of dichloromethane. The combined extracts were washed by saturated NaCl solution, dried over anhydrous sodium sulfate, and evaporated to dryness on a rotary evaporator to afford a colorless oily product, which was 1-{4-chloro-3-[1-(4-ethyoxyphenyl)-1-methoxyethyl]phenyl}-α/β-D-glucopyranose, ESI-MS, m/z=453.4 ([M+1]).

3.13 g of the resulting oily product of 1-{4-chloro-3-[1-(4-ethyoxyphenyl)-1-methoxyethyl]phenyl}-α/β-D-glucopyranose was dissolved in 20 ml of acetic anhydride, and 0.5 g of anhydrous sodium acetate was added. The resulting solution was magnetically stirred and heated to reflux for one hour. After cooling, the mixture was poured into 100 ml of water, stirred overnight at room temperature, and extracted twice with 100 ml of dichloromethane. The combined extracts were washed by saturated NaCl solution, dried over anhydrous sodium sulfate, and evaporated to dryness on a rotary evaporator to afford an off-white solid. After being purified by silica column chromatography, colorless crystals were produced, which was 2,3,4,6-tetra-O-acetyl-1-{4-chloro-3-[(4-ethyoxyphenyl)-1-methoxyethyl]phenyl}-1-deoxy-β-D-glucopyranose. ESI-MS, m/z=621.4 ([M+1]).

4.07 g of the 2,3,4,6-tetra-O-acetyl-1-{4-chloro-3-[1-(4-ethyoxyphenyl)-1-methoxyethyl]phenyl}-1-deoxy-β-D-glucopyranose as above was dissolved in 7 ml of anhydrous methanol containing 0.11 g of sodium methoxide, and stirred for 5 hours at room temperature. And then 1 g of dried strongly acidic resin was added, and stirred overnight at room temperature. The resin was removed by filtration, and the resulting filtrate was evaporated to dryness on a rotary evaporator to afford a white solid, which was 1-{4-chloro-3-[1-(4-ethyoxyphenyl)-1-methoxyethyl]phenyl}-1-deoxy-β-D-glucopyranose. ESI-MS, m/z=453.4 ([M+1]).

Example 52

1-{4-chloro-3-[1-(4-ethyoxyphenyl)-1-fluoroethyl]phenyl}-1-deoxy-β-D-glucopyranose

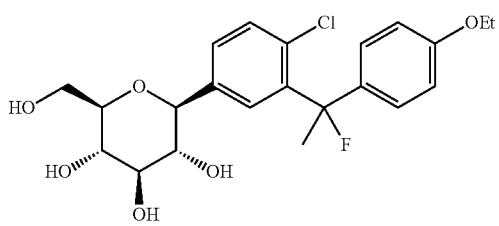 [SMILES: CCOc1ccc(C(C)(F)c2cc([C@@H]3O[C@H](CO)[C@@H](O)[C@H](O)[C@H]3O)ccc2Cl)cc1]

A. 1-(5-bromo-2-chlorophenyl)-1-(4-ethyoxyphenyl)-1-fluoroethane 3.56 g of (5-bromo-2-chlorophenyl)(4-ethyoxyphenyl)(methyl)methanol prepared according to example 36 and 10 ml of anhydrous dichloromethane were added to a 100-ml round-bottomed flask. The resulting solution was cooled in an ice-water bath and magnetically stirred, and then 2 ml of (diethylamino)sulfur trifluoride ($Et_2NSF_3$) was added, and then the reaction mixture was stirred overnight and then poured carefully into 200 ml of ice water. The resulting mixture was extracted twice with 100 ml of dichloromethane. The combined extracts were washed with saturated NaCl solution, dried over anhydrous sodium sulfate, and evaporated to dryness on a rotary evaporator to afford a colorless oily product, which is 1-(5-bromo-2-chlorophenyl)-1-(4-ethyoxyphenyl)-1-fluoroethane. ESI-MS, m/z=357.3 ([M($^{79}$Br)+1]), 359.1 ([M($^{81}$Br)+1]).

B. 1-{4-chloro-3-[1-(4-ethyoxyphenyl)-1-fluoroethyl]phenyl}-1-deoxy-β-D-glucopyranose 3.40 g of 1-(5-bromo-2-chlorophenyl)-1-(4-ethyoxyphenyl)-1-fluoroethane prepared as above, 10 ml of anhydrous THF and a magnetic stirring bar were added into a 100-ml round-bottomed flask. The flask was sealed with a rubber septum, and put in acetone-dry ice system and cooled to −78° C. 10 ml (1.0 M) of n-BuLi was added slowly into the reaction container via syringe while stirring, after which, the mixture was stirred for another one hour in −78° C., and then a solution of 2,3,4,6-tetra-O-trimethylsilylglucolactone as prepared in example 1 in 10 ml of anhydrous toluene was added slowly into the reaction mixture via syringe. After addition, the mixture was stirred for another one hour, and a solution of 1.92 g of methanesulfonic acid in 10 ml of anhydrous methanol was added via syringe, and then the mixture was warmed up to room temperature, and stirred overnight at room temperature. The reaction mixture was poured into saturated NaCl solution, and extracted twice with 100 ml of dichloromethane. The combined extracts were washed by saturated NaCl solution, dried over anhydrous sodium sulfate, and evaporated to dryness on a rotary evaporator to afford a colorless oily product, which was methyl 1-{4-chloro-3-[1-(4-ethyoxyphenyl)-1-fluoroethyl]phenyl}-α/β-D-glucopyranoside, ESI-MS, m/z=471.3 ([M+1]).

3.58 g of the resulting methyl 1-{4-chloro-3-[1-(4-ethyoxyphenyl)-1-fluoroethyl]phenyl}-α/β-D-glucopyranoside was dissolved in 3 ml of anhydrous dichloromethane, and stirred in ice water bath, and then 2 ml of triethylsilane and 1 ml of boron trifluoride diethyl etherate were added sequentially. The reaction mixture was stirred overnight at room temperature, poured carefully into 100 ml of ice water, adjusted to pH=8 with saturated sodium bicarbonate solution, and extracted twice with 100 ml of dichloromethane. The combined extracts were washed by saturated NaCl solution, dried over anhydrous sodium sulfate, and evaporated to dryness on a rotary evaporator to afford a colorless oily product, which was 1-{4-chloro-3-[1-(4-ethyoxylphenyl)-1-fluoroethyl]phenyl}-α/β-D-glucopyranose. ESI-MS, m/z=441.2 ([M+1]).

3.02 g of the resulting colorless oily product of 1-{4-chloro-3-[1-(4-ethyoxyphenyl)-1-fluoroethyl]phenyl}-α/β-D-glucopyranose was dissolved in 20 ml of acetic anhydride, and then 0.5 g of anhydrous sodium acetate was added. The resulting solution was magnetically stirred and heated to reflux for one hour. After cooling, the mixture was poured into 100 ml of water, stirred overnight at room temperature, and extracted twice with 100 ml of dichloromethane. The combined extracts were washed with saturated NaCl solution, dried over anhydrous sodium sulfate, and evaporated to dryness on a rotary evaporator to afford an off-white solid. After being purified by silica column chromatography, colorless crystals were produced, which was 2,3,4,6-tetra-O-acetyl-1-{4-chloro-3-[1-(4-ethyoxyphenyl)-1-fluoroethyl]phenyl}-1-deoxy-β-D-glucopyranose, ESI-MS, m/z=609.2 ([M+1]).

3.98 g of the 2,3,4,6-tetra-O-acetyl-1-{4-chloro-3-[1-(4-ethyoxyphenyl)-1-fluoroethyl]phenyl}-1-deoxy-β-D-glucopyranose prepared as above was dissolved in 7 ml of anhydrous methanol containing 0.11 g of sodium methoxide, and stirred for 5 hours at room temperature, and then 1 g of dried strongly acidic resin was added, and stirred overnight at room temperature. The resin was removed by filtration, and the resulting filtrate was evaporated to dryness on a rotary evaporator to afford a white solid, which was 1-{4-chloro-3-[(4-ethyoxyphenyl)-1-fluoroethyl]phenyl}-1-deoxy-β-D-glucopyranose. ESI-MS, m/z=441.2 ([M+1]).

Example 53

1-{4-chloro-3-[1-(4-ethyoxyphenyl)(methoxyl)methyl]phenyl}-1-deoxy-β-D-glucopyranose

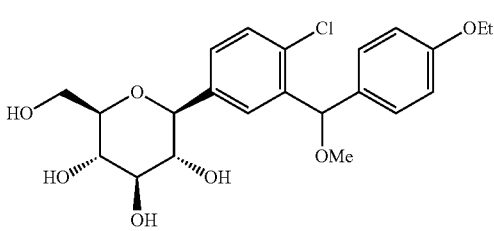 [SMILES: CCOc1ccc(C(OC)c2cc([C@@H]3O[C@H](CO)[C@@H](O)[C@H](O)[C@H]3O)ccc2Cl)cc1]

A. (5-bromo-2-chlorophenyl)(4-ethyoxyphenyl)(methoxy)ethane 3.42 g of (5-bromo-2-chlorophenyl)(4-ethyoxyphenyl)methanol prepared according to example 1 and 10 ml of anhydrous THF were added into a 100-ml round-bottomed flask, and the resulting solution was cooled in ice-water bath and magnetically stirred. 0.40 g (60%) of solid NaH was added in portions, after which, the resulting mixture was stirred for another one hour, and then 1.70 g of dried MeI was added. The reaction mixture was stirred overnight at room temperature, poured carefully into 200 ml of ice water, and adjusted pH to 4-5 with concentrated hydrochloric acid. The resulting acidic mixture was extracted twice with 100 ml of dichloromethane. The combined extracts were washed with saturated NaCl solution, dried over anhydrous sodium sulfate, and evaporated to dryness on a rotary evaporator to afford a colorless oily product, which was (5-bromo-2-chlorophenyl)(4-ethyoxyphenyl)(methoxy)methane. ESI-MS, m/z=355.2 ([M($^{79}$Br)+1]), 357.2 ([M($^{81}$Br)+1]).

B. 1-{4-chloro-3-[(4-ethyoxyphenyl)(methoxy)methyl]phenyl}-1-deoxy-β-D-glucopyranose 3.20 g of (5-bromo-2-chlorophenyl)(4-ethyoxyphenyl)(methoxy)methane prepared as above, 10 ml of anhydrous THF and a magnetic stirring bar were added into a 100-ml round-bottomed flask, and then the flask was sealed by a rubber septum, and put in acetone-dry ice system and cooled to −78° C. 10 ml (1.0 M) of n-BuLi was added slowly into the reaction mixture via syringe while stirring, after which, the mixture was stirred for another one hour in −78° C. And then a solution of the 2,3,4,6-tetra-O-trimethylsilyl glucolactone prepared according to example 1 in 10 ml of anhydrous toluene was added slowly into the reaction container via syringe. After addition, the mixture was stirred for another one hour, and a solution of 1.92 g methanesulfonic acid in 10 ml of anhydrous methanol was added via a syringe, and then the mixture was warmed up to room temperature, and stirred overnight at room temperature. The reaction mixture was poured into saturated NaCl solution, and was extracted twice with 100 ml of dichloromethane. The combined extracts were washed with saturated NaCl solution, dried over anhydrous sodium sulfate, and evaporated to dryness on a rotary evaporator to afford a colorless oily product, which was methyl 1-{4-chloro-3-[1-(4-ethyoxyphenyl)(methoxy)methyl]phenyl}-α/β-D-glucopyranoside. ESI-MS, m/z=469.3 ([M+1]).

3.63 g of the resulting methyl 1-{4-chloro-3-[(4-ethyoxyphenyl)(methoxy)methyl]phenyl}-α/β-D-glucopyranoside was dissolved in 3 ml of anhydrous dichloromethane, and stirred in ice water bath, and 2 ml of triethylsilane and 1 ml of boron trifluoride diethyl etherate were added sequentially. The reaction mixture was stirred overnight at room temperature, poured carefully into 100 ml of ice water, adjusted to pH=8 with saturated sodium bicarbonate solution, and extracted twice with 100 ml of dichloromethane. The combined extracts were washed with saturated NaCl solution, and dried over anhydrous sodium sulfate, evaporated to dryness on a rotary evaporator to afford a colorless oily product, which was 1-{4-chloro-3-[(4-ethyoxyphenyl)(methoxyl)methyl]phenyl}-α/β-D-glucopyranose. ESI-MS, m/z=439.1 ([M+1]).

3.13 g of the resulting colorless oily product of 1-{4-chloro-3-[(4-ethyoxyphenyl)(methoxy)methyl]phenyl}-α/β-D-glucopyranose was dissolved in 20 ml of acetic anhydride, and 0.5 g of anhydrous sodium acetate was added. The resulting solution was magnetically stirred and heated to reflux for one hour. After cooling, the mixture was poured into 100 ml of water, stirred overnight at room temperature, extracted twice with 100 ml of dichloromethane. The combined extracts were washed once by saturated NaCl solution, dried over anhydrous sodium sulfate, and evaporated to dryness on a rotary evaporator to afford an off-white solid. After being purified by silica column chromatography, colorless crystals were produced, which were 2,3,4,6-tetra-O-acetyl-1-{4-chloro-3-[(4-ethyoxyphenyl)(methoxyl)methyl]phenyl}-1-deoxy-β-D-glucopyranose, ESI-MS, m/z=607.3 ([M+1]).

4.10 g of the 2,3,4,6-tetra-O-acetyl-1-{4-chloro-3-[(4-ethyoxyphenyl)(methoxyl)methyl]phenyl}-1-deoxy-β-D-glucopyranose prepared as above was dissolved in 7 ml of anhydrous methanol containing 0.11 g of sodium methoxide, and stirred for 5 hours at room temperature, and then 1 g of dried strongly acidic resin was added, and stirred overnight at room temperature. The resin was removed by filtration, and the resulting filtrate was evaporated to dryness on a rotary evaporator to afford a white solid, which was 1-{4-chloro-3-[1-(4-ethyoxyphenyl)(methoxy)methyl]phenyl}-1-deoxy-β-D-glucopyranose. ESI-MS, m/z=439.1 ([M+1]).

Example 54

|  | dosage/pill |
|---|---|
| Sample from example 2 | 10 mg |
| Microcrystalline cellulose | 80 mg |
| Pregelatinized starch | 70 mg |
| Polyvinylpyrrolidone | 6 mg |
| Carboxymethyl starch sodium | 5 mg |
| Magnesium stearate | 2 mg |
| Talc powder | 2 mg |

The active ingredient, pregelatinized starch and microcrystalline cellulose were screened and mixed thoroughly. Polyvinylpyrrolidone solution was added, and the resulting mixture was mixed and prepared into a damp mass, then it was screened and prepared into wet granules, and then was dried at 50-60° C. The carboxymethyl starch sodium, magnesium stearate and talc powder were screened in advance, and were added into the granules as above for tabletting.

Example 55

|  | dosage/pill |
| --- | --- |
| Sample from example 1 | 10 mg |
| Microcrystalline cellulose | 80 mg |
| Pregelatinized starch | 70 mg |
| Polyvinylpyrrolidone | 6 mg |
| Carboxy methyl starch sodium | 5 mg |
| Magnesium stearate | 2 mg |
| Talc powder | 2 mg |

The active ingredient, pregelatinized starch and microcrystalline cellulose were screened and mixed thoroughly. Polyvinylpyrrolidone solution was added, and the resulting mixture was mixed and prepared into a damp mass, then it was screened and prepared into wet granules, and then was dried at 50-60° C. Carboxy methyl starch sodium salt, magnesium stearate and talc powder were screened in advance, and were added into the granules as above for tabletting.

Example 56

|  | dosage/pill |
| --- | --- |
| Sample from example 16 | 10 mg |
| Microcrystalline cellulose | 30 mg |
| Pregelatinized starch | 20 mg |
| Polyvinylpyrrolidone | 3 mg |
| Magnesium stearate | 2 mg |
| Ttalc powder | 1 mg |

The active ingredient, pregelatinized starch and microcrystalline cellulose were screened and mixed thoroughly. Polyvinylpyrrolidone solution was added, and the resulting mixture was mixed and prepared into a damp mass, then it was screened and prepared into wet granules, and then was dried at 50-60° C. Magnesium stearate and talc powder were screened in advance, and then were added into the granules as above and the resulting mixture was filled into capsules.

Example 57

|  | dosage/pill |
| --- | --- |
| Sample from example 31 | 10 mg |
| Microcrystalline cellulose | 30 mg |
| Pregelatinized starch | 20 mg |
| Polyvinylpyrrolidone | 3 mg |
| Magnesium stearate | 2 mg |
| Talc powder | 1 mg |

The active ingredient, pregelatinized starch and microcrystalline cellulose were screened and mixed thoroughly. Polyvinylpyrrolidone solution was added, and the resulting mixture was mixed and prepared into a damp mass, then it was screened and prepared into wet granules, and then was dried at 50-60° C. Magnesium stearate and talc powder were screened in advance, and then were added into the granules as above and the resulting mixture was filled into capsules.

Example 58

|  | dosage/50 ml |
| --- | --- |
| Sample from example 45 | 10 mg |
| Citric acid | 100 mg |
| NaOH | appropriate amount (to pH 4.0-5.0) |
| Distilled water | 50 ml |

Firstly, citric acid was added into distilled water. After stirring and dissolving, the sample was added. The solution was slightly heated for dissolving, and adjusted to pH 4.0-5.0. 0.2 g activated carbon was added, and the solution was stirred for 20 min at room temperature, and then filtered. The concentration of the filtrate was controlled and measured, and then the filtrate was packed by 5 ml per ampoules, and sterile for 30 min at a high temperature. Thus the injections are obtained.

Example 59

|  | dosage/50 ml |
| --- | --- |
| Sample from example 46 | 10 mg |
| Citric acid | 100 mg |
| NaOH | appropriate amount (to pH 4.0-5.0) |
| Distilled water | 50 ml |

Firstly, citric acid was added into distilled water. After stirring and dissolving, the sample was added. The solution was slightly heated for dissolving, and adjusted to pH 4.0-5.0. 0.2 g activated carbon was added, and the solution was stirred for 20 min at room temperature, and then filtered. The concentration of the filtrate was controlled and measured, and then the filtrate was packed by 5 ml per ampoules, and sterile for 30 min at a high temperature. Thus the injections are obtained.

Example 60

| Sample from example 47 | 3.0 g |
| --- | --- |
| Poloxamer | 1.0 g |
| Sodium hydroxide | 0.2 g |
| Citric acid | QS |
| Mannitol | 26.0 g |
| Lactose | 23.0 g |
| Water for injection | 100 ml |

Preparation process: the main medicine, mannitol, lactose and poloxamer were added into 80 ml water for injection, and stirred for dissolving. 1 mol/l citric acid was added to adjust the pH to 7.0-9.0, and water was added up to 100 ml. 0.5 g active carbon was added and the resulting mixture was stirred for 20 min at 30° C., and then decarbonized. Millipore filter was used to filter out the bacteria. The filtrate was packed by 1 ml per strip. After frozen for 2 hours, the samples were hypobaric dried for 12 hours under freezing. After the temperature of the samples returned to room temperature, they were dried for another 5 hours, producing white loose blocks, which were sealed before it was done.

Example 61

| | |
|---|---|
| Granules | 100 bags |
| Sample from example 48 | 30.0 g |
| Lactose | 55.0 g |
| Mannitol | 14.0 g |
| Aspartame | 0.05 g |
| Essence | 0.05 g |
| 2% hydroxypropyl methylcellulose (prepared with pure water) | QS |

Preparation process: the main medicine and auxiliary material were screened by a 100-mesh screen and mixed thoroughly, and then prescription dose of auxiliary material was measured and mixed thoroughly with the main medicine. Adhesive was added, and then the mixture was prepared into a damp mass and granulated using a 14-mesh screen, dried at 55° C., and screened for regulation by a 12-mesh screen. The weights of the bags were measured and then packaged them.

Example 62

A suspension of the test compounds with 5 mg/ml was prepared by dissolving the sample in 1% sodium carboxymethylcellulose solution. The administration dosage is 0.2 ml/20 g body weight, which equals to a dosage of 10 mg/kg.

Female and male of healthy ICR mice are half to half, and the weight is 20-24 g, in accordance with standard level one. Animals were fasted for 16 hours. 2 g/kg glucose in saline was intraperitoneally injected 2 hours after the test compounds (for Dapagliflozin, glucose was injected 1.5 hours after medicine), and blood samples were collected from mice tall vein using capillary at fixed times of 0.5 h, 1 h, 2 h, 3 h and 4 h after challenging with glucose. The sera were separated using centrifugation. The glucose oxidase method was used to measure glucose content of serum at different time points. The results are showed in the following table.

| Groups | dosage (mg/kg) | blood glucose at 0.5 h (mg/dl) | blood glucose at 1 h (mg/dl) | blood glucose at 2 h (mg/dl) | blood glucose at 3 h (mg/dl) | blood glucose at 4 h (mg/dl) |
|---|---|---|---|---|---|---|
| models | — | 431.2 ± 44.2 | 283.1 ± 35.1 | 178.8 ± 21.1 | 112.0 ± 11.4 | 85.1 ± 11.2 |
| Dapagliflozin | 10 | 277.1 ± 42.4 | 172.1 ± 34.1 | 92.1 ± 21.1 | 81.3 ± 20.1 | 60.0 ± 11.0 |
| Sample from example 1 | 10 | 194.1 ± 41.3 | 161.1 ± 35.4 | 97.3 ± 31.2 | 69.1 ± 22.1 | 67.2 ± 17.1 |
| Sample from example 16 | 10 | 157.1 ± 21.3 | 137.0 ± 27.7 | 102.4 ± 17.5 | 88.1 ± 32.2 | 70.3 ± 14.2 |
| Sample from example 36 | 10 | 189.1 ± 21.2 | 120.1 ± 10.2 | 113.0 ± 11.0 | 74.6 ± 21.0 | 69.1 ± 13.2 |
| Sample from example 50 | 10 | 288.0 ± 40.0 | 191.3 ± 22.1 | 160.6 ± 20.3 | 113.3 ± 13.3 | 87.3 ± 15.0 |
| Sample from example 51 | 10 | 250.5 ± 33.1 | 158.2 ± 20.6 | 123.2 ± 33.1 | 101.2 ± 11.7 | 75.5 ± 21.4 |
| Sample from example 52 | 10 | 209.3 ± 30.4 | 175.1 ± 20.5 | 158.6 ± 31.1 | 101.2 ± 12.4 | 80.0 ± 13.2 |
| Sample from example 53 | 10 | 199.0 ± 21.3 | 171.4 ± 36.1 | 110.2 ± 20.8 | 93.0 ± 17.7 | 69.6 ± 17.3 |

The results indicate that every compound can significantly improve the glucose tolerance.

The invention claimed is:

1. A compound with the structure of general formula I or a pharmaceutically acceptable salt or prodrug ester thereof:

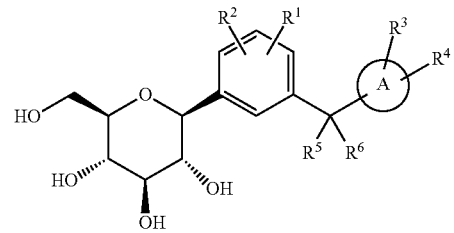

wherein, $R^1$, $R^2$, $R^3$, $R^4$ are independently selected from the group consisting of H, F, Cl, Br, I, OH, $OR^7$, $SR^8$, $OCF_3$, $CF_3$, $CHF_2$, $CH_2F$, a $C_1$-$C_3$ alkyl and a cycloalkyl having 3 to 5 carbon atoms, wherein $R^7$ and $R^8$ are independently selected from a $C_1$-$C_3$ alkyl, and both of the aforesaid alkyl and cycloalkyl are optionally substituted by one or more atoms selected from F and Cl;

ring A is selected from an aromatic monocycle and an aromatic bicycle, and the two rings in the aromatic bicycle are either fused to form a fused ring or connected through a covalent bond as two independent aromatic rings; both the aromatic monocycle and the aromatic bicycle are a 5- to 12-membered ring which is optionally substituted by 1 to 3 heteroatoms selected from O, S and N; ring A is connected with other part of compound I through any position of ring A;

the definitions of $R^5$ and $R^6$ are selected from the following:

(1) $R^5$=$R^6$=Me;
(2) $R^5$=Me, $R^6$=OMe;
(3) $R^5$=Me, $R^6$=H;
(4) $R^5$=Me, $R^6$=F;
(5) $R^5$=F, $R^6$=H;
(6) $R^5$=OMe, $R^6$=H.

2. The compound with the structure of general formula I or a pharmaceutically acceptable salt or prodrug ester thereof according to claim 1, wherein, $R^1$, $R^2$, $R^3$, $R^4$ are independently selected from the group consisting of H, F, Cl, $OR^7$, $SR^8$, $OCF_3$, $CF_3$, $CHF_2$, $CH_2F$, a $C_1$-$C_3$ alkyl and a cycloalkyl having 3 to 5 carbon atoms, wherein $R^7$ and $R^8$ are independently selected from a $C_1$-$C_3$ alkyl, and both of the aforesaid alkyl and cycloalkyl are optionally substituted by one or more atoms selected from F and Cl;

ring A is selected from an aromatic monocycle and an aromatic bicycle; both the aromatic monocycle and aromatic bicycle are a 5- to 12-membered ring which is optionally substituted by 1 to 2 heteroatoms selected from O and S; ring A is connected with other part of compound I through any position of ring A;

the definitions of $R^5$ and $R^6$ are selected from the following:
(1) $R^5=R^6=$Me;
(2) $R^5=$Me, $R^6=$H;
(3) $R^5=$Me, $R^6=$F;
(4) $R^5=$F, $R^6=$H.

3. The compound with the structure of general formula I or a pharmaceutically acceptable salt or prodrug ester thereof according to claim 1, wherein, $R^1$, $R^2$, $R^3$, $R^4$ are independently selected from the group consisting of F, Cl, $OR^7$, $SR^8$, $OCF_3$, $CF_3$, $CHF_2$, $CH_2F$, a $C_1$-$C_3$ alkyl and a cycloalkyl having 3 to 4 carbon atoms, wherein $R^7$ and $R^8$ are independently selected from a $C_1$-$C_3$ alkyl, and both of the aforesaid alkyl and cycloalkyl are optionally substituted by one or more F atoms;

ring A is selected from the group consisting of benzene ring, benzothiophene ring, benzofuran ring, azulene, benzene ring and thiophene ring connected by a covalent bond in any possible form, and benzene ring and furan ring connected by a covalent bond in any possible form, ring A is connected to other part of compound I through any position of ring A;

the definitions of $R^5$ and $R^6$ are selected from the following:
(1) $R^5=R^6=$Me;
(2) $R^5=$Me, $R^6=$H;
(3) $R^5=$F, $R^6=$H.

4. The compound with the structure of general formula I or a pharmaceutically acceptable salt or prodrug ester thereof according to claim 1, wherein the structure of the compound is selected from the group consisting of:

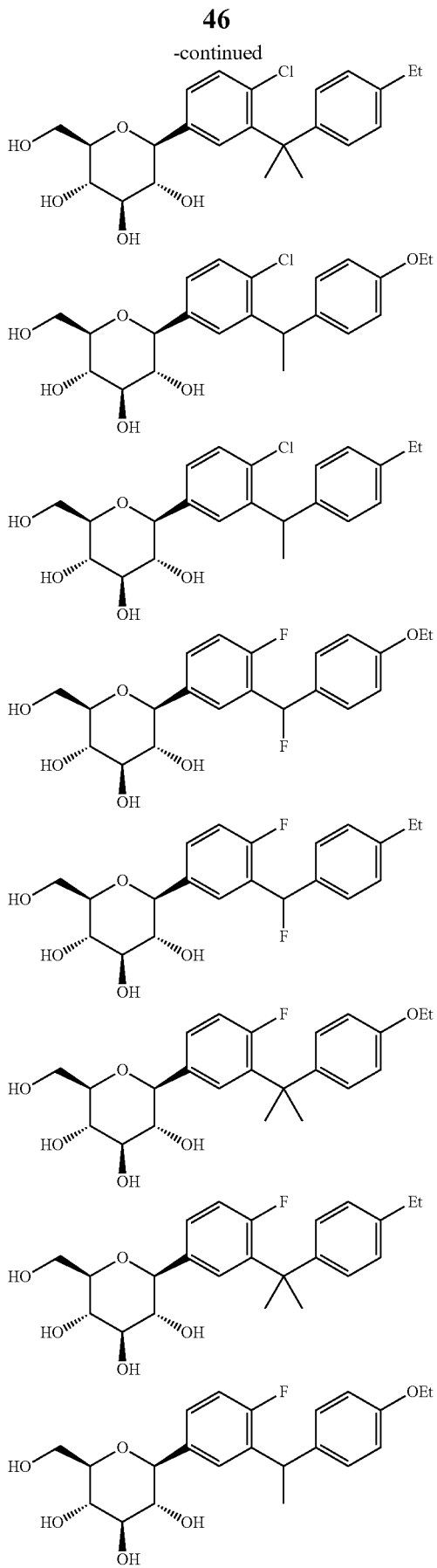

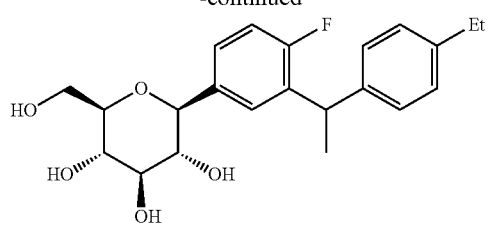
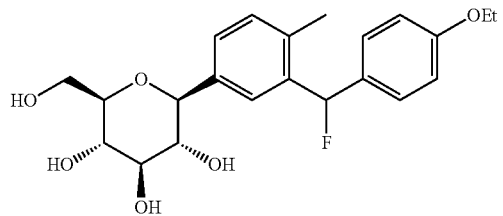
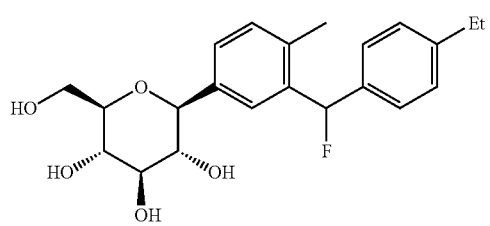
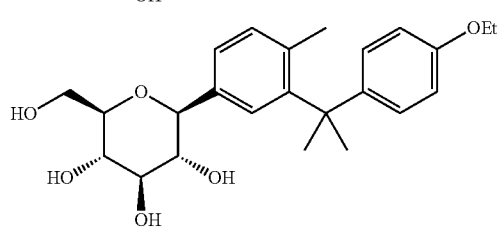
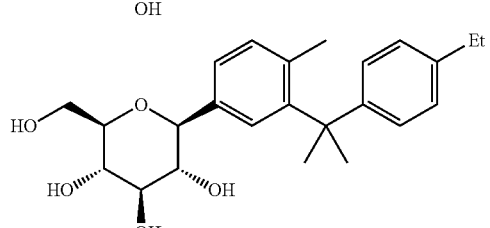
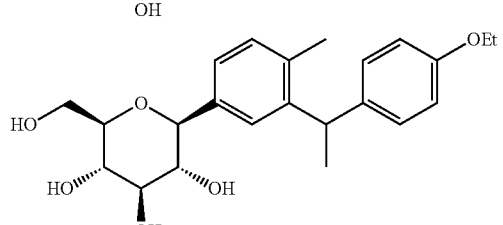
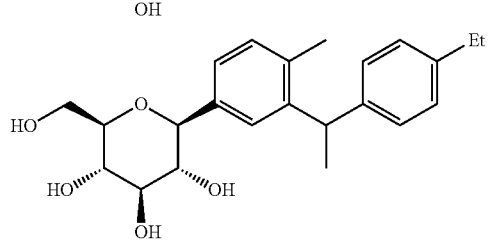
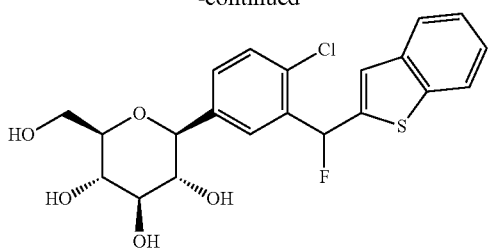
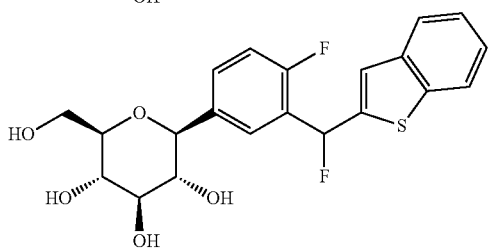
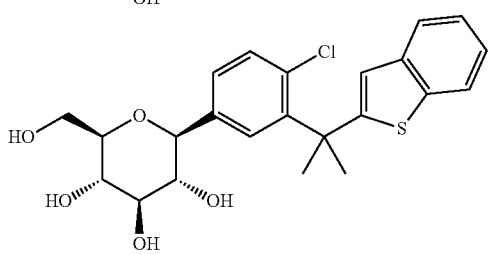
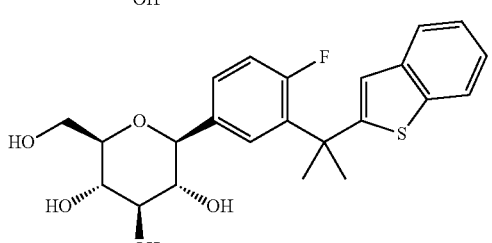
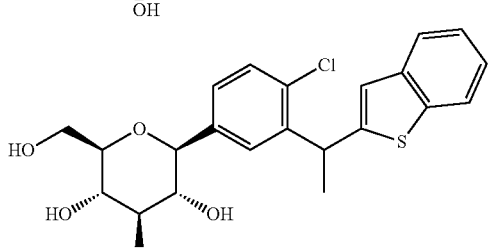
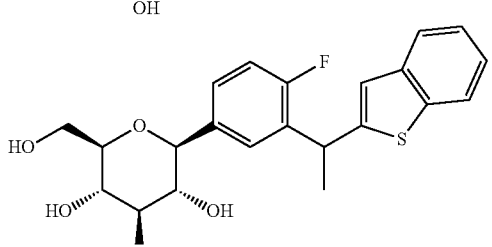
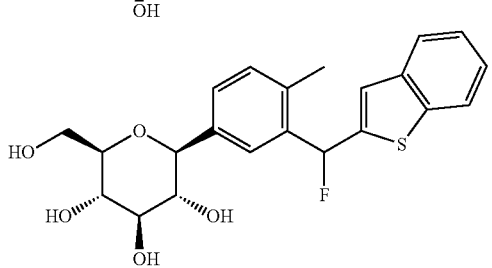

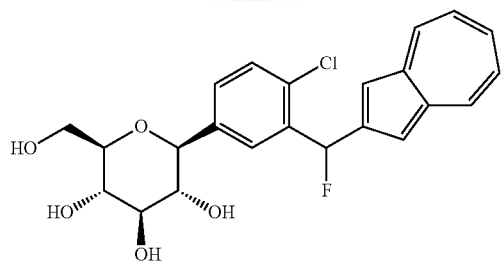
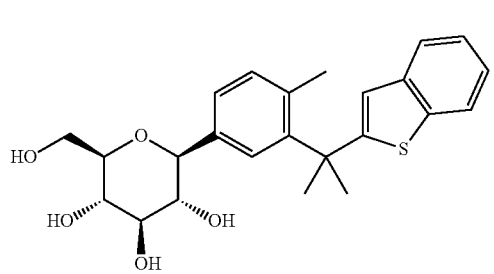
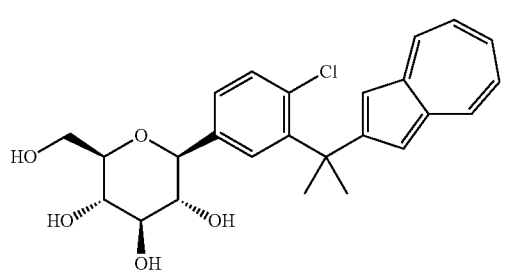
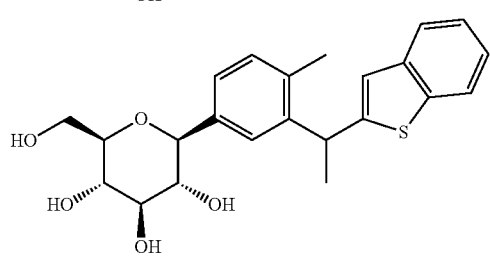
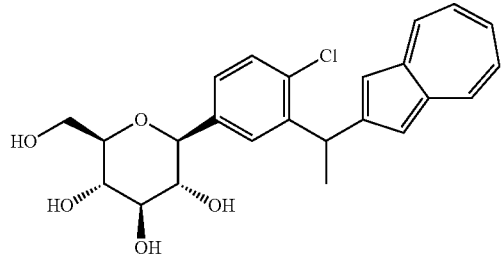
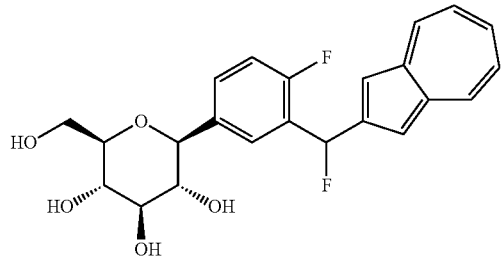
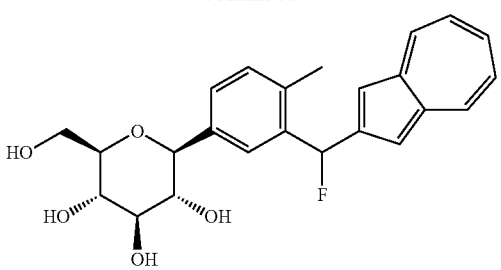
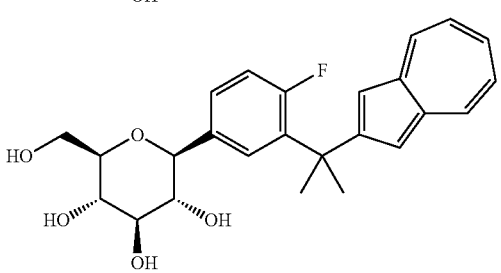
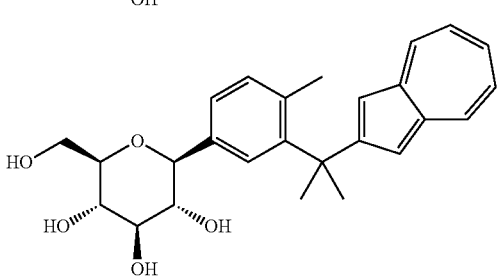
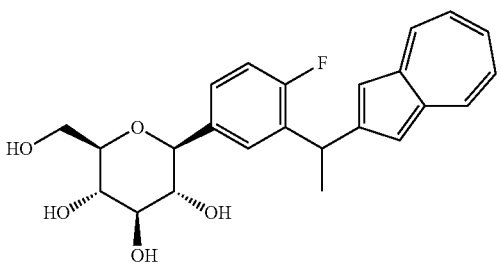
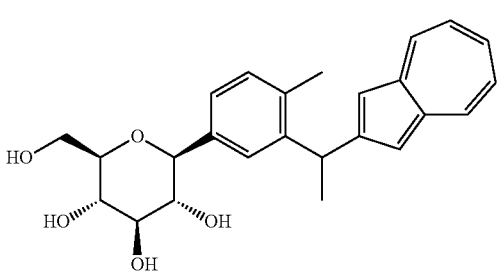
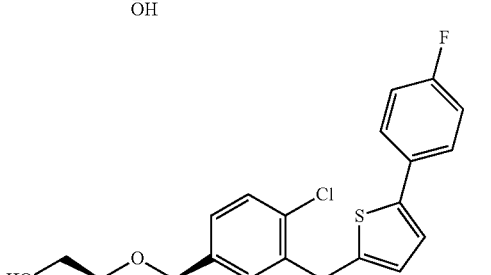

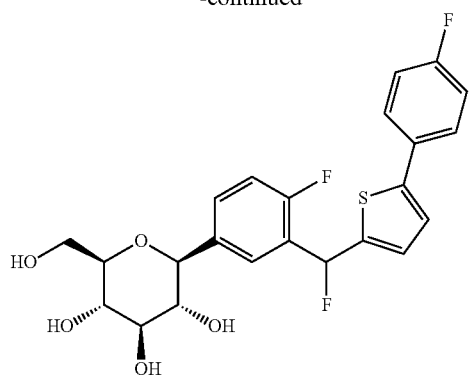

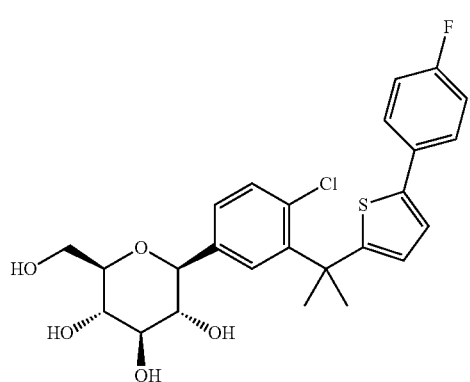

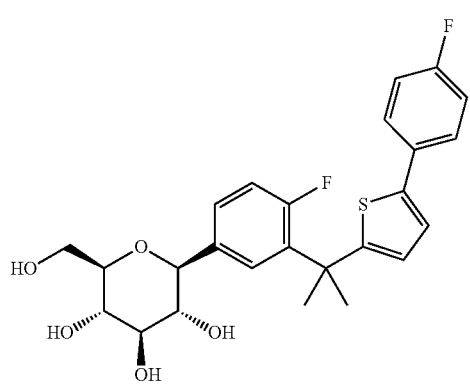

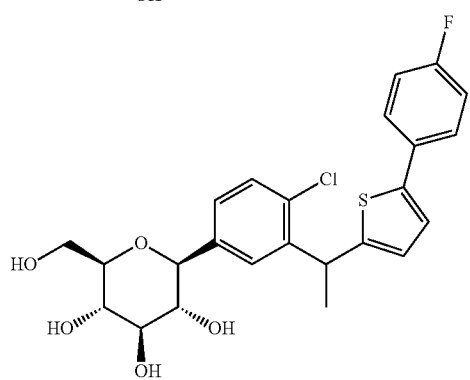

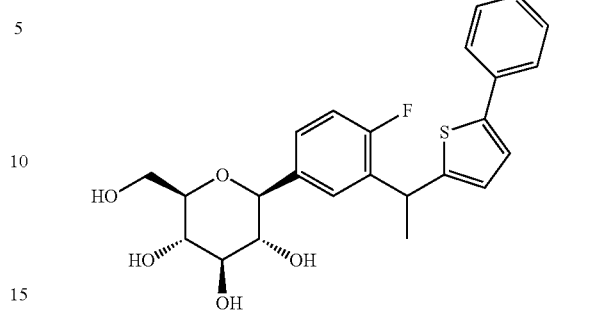

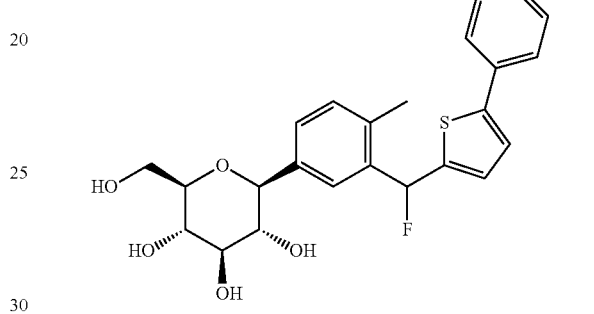

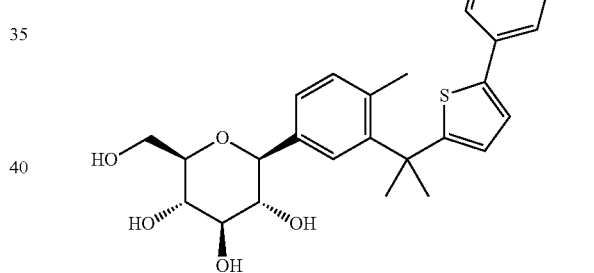

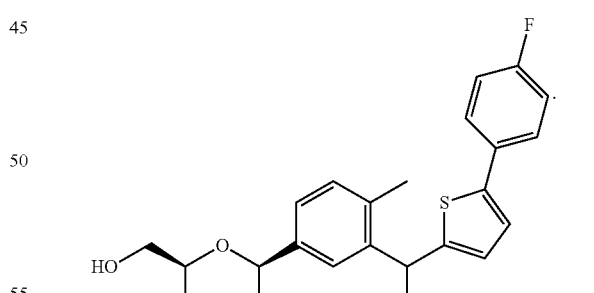 and

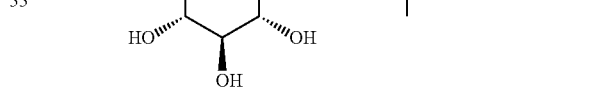
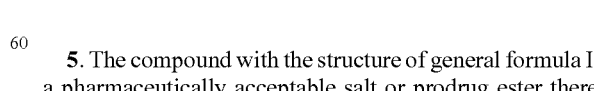
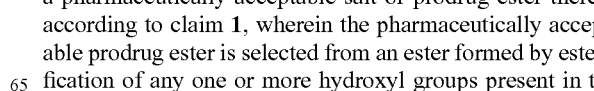
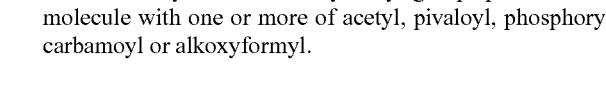

5. The compound with the structure of general formula I or a pharmaceutically acceptable salt or prodrug ester thereof according to claim 1, wherein the pharmaceutically acceptable prodrug ester is selected from an ester formed by esterification of any one or more hydroxyl groups present in the molecule with one or more of acetyl, pivaloyl, phosphoryl, carbamoyl or alkoxyformyl.

6. A method for preparing a compound with the structure of general formula I or a pharmaceutically acceptable salt or prodrug ester thereof according to claim 1, the method comprising the steps of:

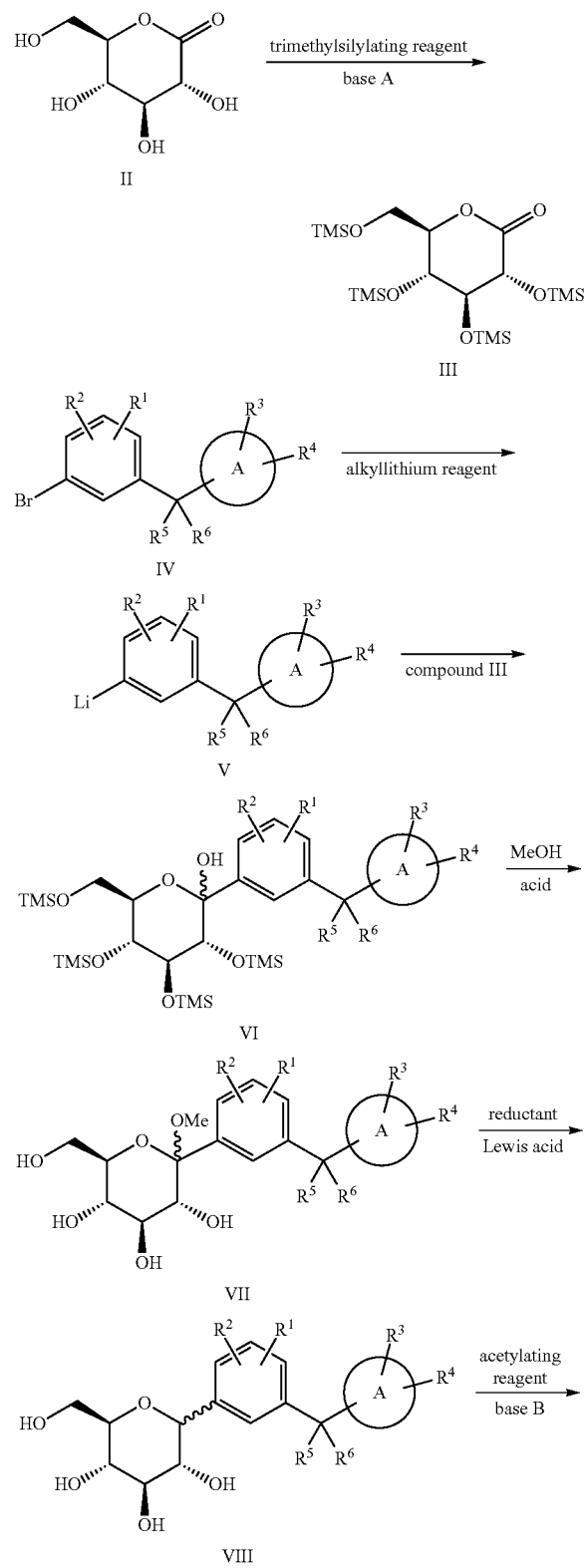

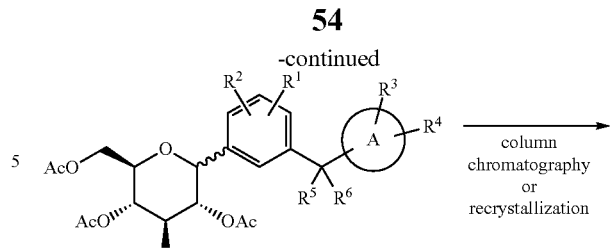

wherein the base A is selected from N-methylmorpholine, triethylamine, pyridine and 4-dimethylaminopyridine; the base B is selected from anhydrous sodium acetate, pyridine and 4-dimethylaminopyridine and the base C is selected from sodium methoxide, NaOH and KOH.

7. The method according to claim 6, wherein the trimethylsilylating reagent is trimethylchlorosilane; the alkyllithium reagent is n-butyllithium; the acid is selected from methanesulfonic acid, trifluoromethanesulfonic acid and p-toluenesulfonic acid; the Lewis acid is selected from $BF_3.Et_2O$, $BF_3.MeCN$ and trifluoroacetic acid; the reductant is selected from triethyl silane and triisopropylsilane; and the acetylating reagent is selected from acetic anhydride and acetyl chloride.

8. The method according to claim 6, wherein, (1) when $R^5=R^6=Me$, the compound IV is IV-1,

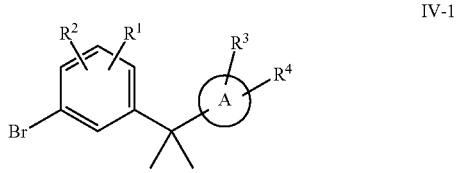

wherein the compound IV-1 is synthesized by the following route,

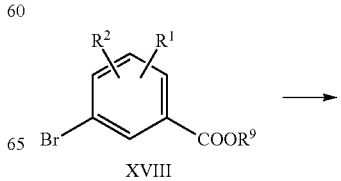

-continued

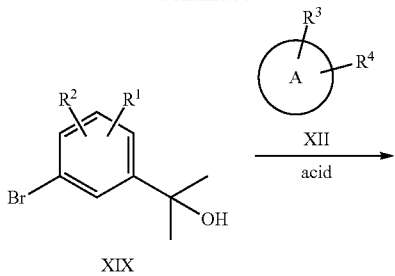

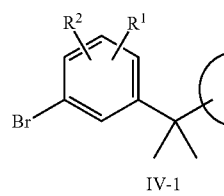

wherein compound XVIII is treated with MeLi, MeMgI or MeMgBr to produce compound XIX; compound XIX reacts with compound XII in the presence of an acid to produce compound IV-1, wherein the acid is methanesulfonic acid, trifluoromethanesulfonic acid, p-toluenesulfonic acid or concentrated sulfuric acid; or (2) when $R^5$=Me, $R^6$=OMe, the compound IV is IV-2,

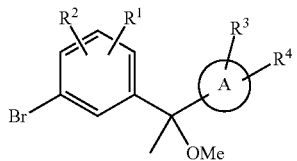

wherein the compound IV-2 is synthesized by the following route,

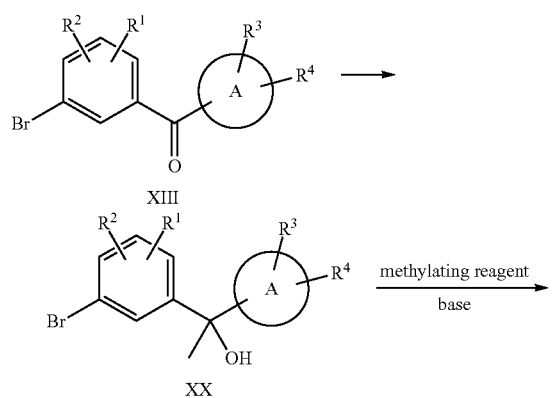

wherein compound XIII is treated with MeLi, MeMgI or MeMgBr to produce compound XX; compound XX is treated with a methylating reagent in the presence of a base to produce compound IV-2, wherein the base is NaH, KH or NaNH$_2$; and the methylating reagent is Me$_2$SO$_4$ or MeI;

alternatively, the compound XX is synthesized by the following route,

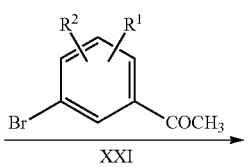

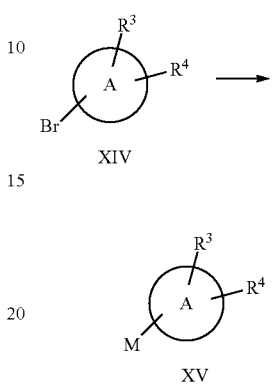

wherein compound XIV is treated with n-BuLi or metal Mg to produce compound XV; compound XV reacts with compound XXI to produce compound XX; or, (3) when $R^5$=Me, $R^6$=H, the compound IV is IV-3,

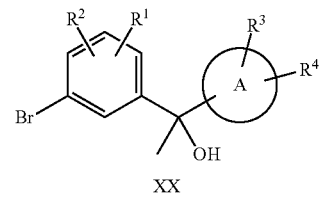

wherein the compound IV-3 is synthesized by the following route,

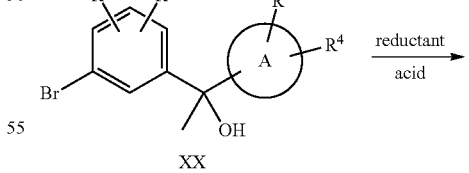

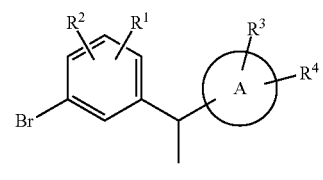

wherein compound XX is reduced to compound IV-3 by a reductant in the presence of an acid, wherein the acid is BF$_3$.Et$_2$O or trifluoroacetic acid, and the reductant is triethylsilane or triisopropylsilane; or (4) when R$^5$=Me, R$^6$=F, the compound is IV-4,

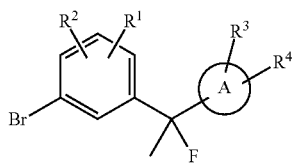

IV-4 wherein the compound IV-4 is synthesized by the following route,

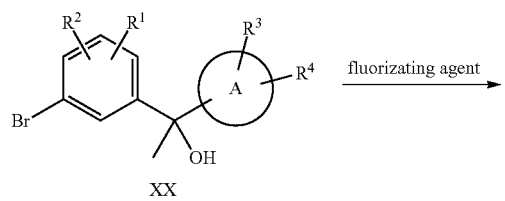 fluorizating agent 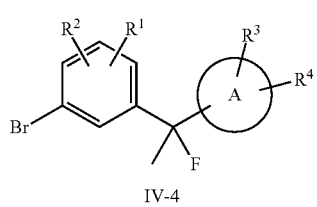

XX
IV-4 wherein compound XX reacts with a fluorinating agent to produce compound IV-4, wherein the fluorinating agent is SF$_4$ or Et$_2$NSF$_3$; or (5) when R$^5$=F, R$^6$=H, the compound IV is IV-5,

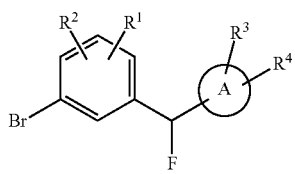

IV-5 wherein the compound IV-5 is synthesized by the following route,

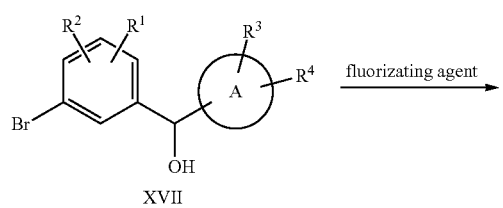 fluorizating agent

XVII

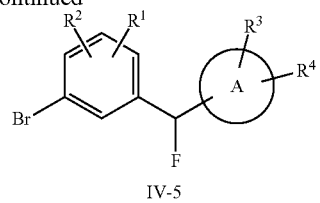

IV-5 wherein compound XVII reacts with a fluorinating agent to produce compound IV-5, wherein the fluorinating agent is SF$_4$ or Et$_2$NSF$_3$; wherein, the compound XVII is produced by reducing compound XIII through the following reaction, and the reductant is selected from NaBH$_4$, KBH$_4$, LiAlH$_4$ and LiBH$_4$; or

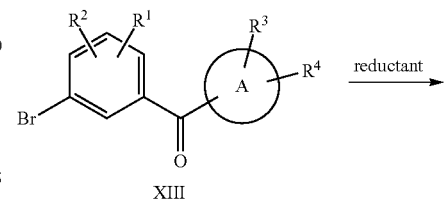 reductant

XIII

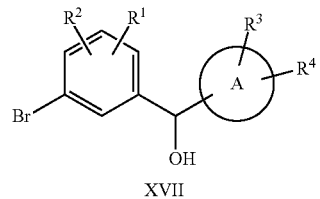

XVII (6) when R$^5$=OMe, R$^6$=H, the compound IV is IV-6,

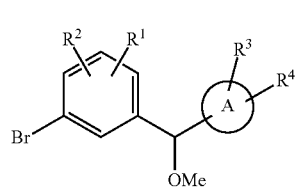

IV-6 wherein the compound IV-6 is synthesized by the following route,

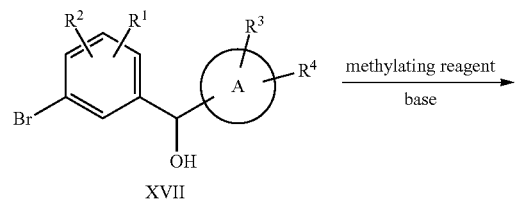 methylating reagent / base

XVII

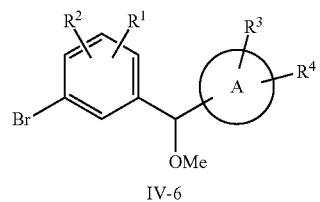

IV-6 wherein compound XVII is treated with a methylating reagent in the presence of a base to produce compound IV-6, wherein the base is NaH, KH or NaNH$_2$, and the methylating reagent is Me$_2$SO$_4$ or MeI.

9. The method according to claim 6, wherein the method comprises the steps of:

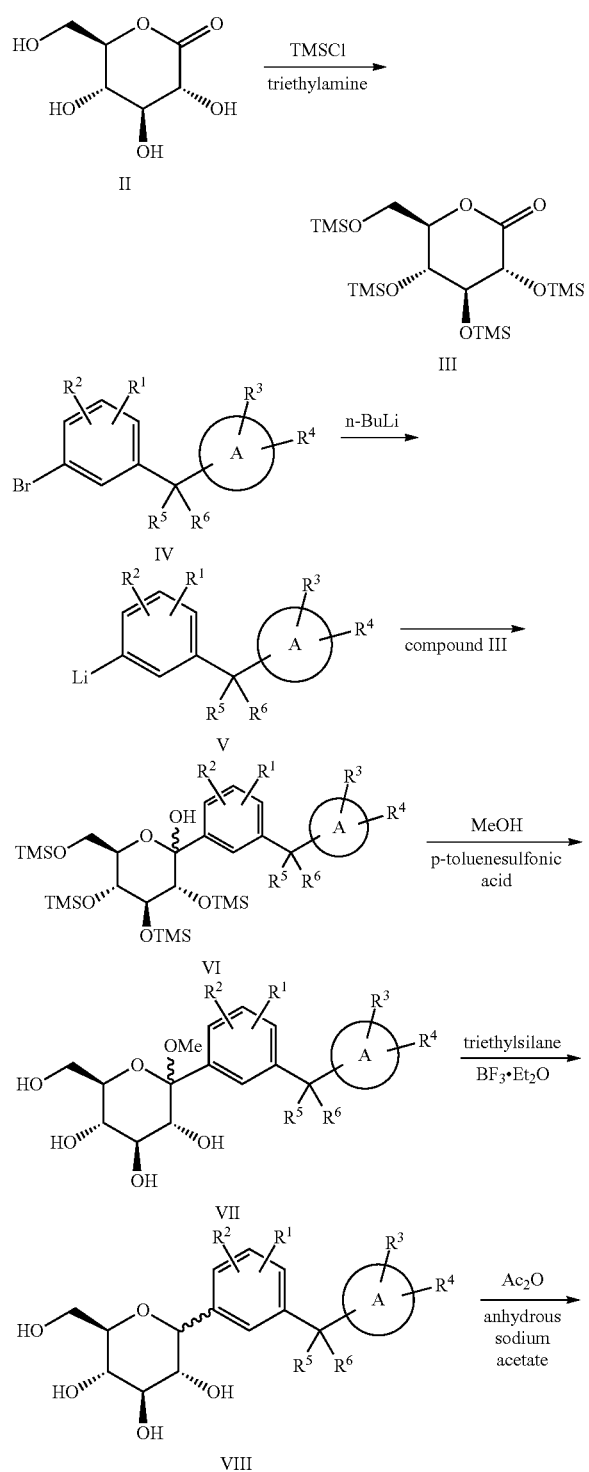

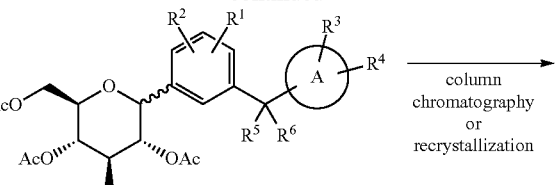

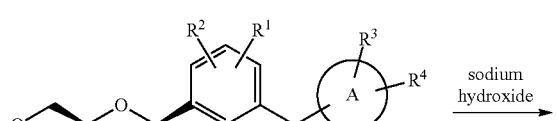

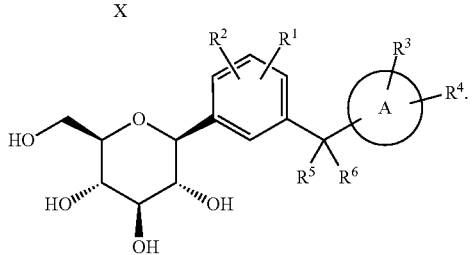

10. A method for treating diabetes, which comprises administering to a patient in need thereof an effective amount of a compound with the structure of general formula I or a pharmaceutically acceptable salt or prodrug ester thereof according to claim 1.

11. A pharmaceutical composition, which comprises a compound with the structure of general formula I or a pharmaceutically acceptable salt or prodrug ester thereof according to claim 1 and a pharmaceutically acceptable carrier and/or excipient.

12. The pharmaceutical composition according to claim 11, wherein the pharmaceutical composition is a solid oral preparation, a liquid oral preparation or an injectable preparation.

13. The pharmaceutical composition according to claim 12, wherein the solid oral preparation and liquid oral preparation are selected from a dispersible tablet, an enteric-coated tablet, a chewable tablet, an orally disintegrating tablet, a capsule, a granule and an oral solution; and the injectable preparation includes a vial injection, a freeze-dried powder for injection, a large volume infusion or a small volume infusion.

14. A method for inhibiting sodium glucose cotransporter 2, which comprises administering to a patient in need thereof an effective amount of a compound with the structure of general formula I or a pharmaceutically acceptable salt or prodrug ester thereof according to claim 1.

* * * * *